United States Patent [19]

Iwane et al.

[11] Patent Number: 5,639,664

[45] Date of Patent: Jun. 17, 1997

[54] METHOD FOR PRODUCING HUMAN NERVE GROWTH FACTOR 2

[75] Inventors: Makoto Iwane, Brookline, Mass.; Yoshihiko Kaisho, Osaka; Koichi Igarashi, Kyoto, both of Japan

[73] Assignee: Takeda Chemical Industries, Ltd., Osaka, Japan

[21] Appl. No.: 376,296

[22] Filed: Jan. 23, 1995

Related U.S. Application Data

[63] Continuation of Ser. No. 154,697, Nov. 18, 1993, abandoned, which is a continuation of Ser. No. 834,676, Feb. 12, 1992, abandoned.

[30] Foreign Application Priority Data

Feb. 18, 1991  [JP]  Japan ..................... 3-023579

[51] Int. Cl.$^6$ .............. C12N 15/79; C12N 1/16; C12N 5/10; C12N 21/00
[52] U.S. Cl. ............... 435/320; 435/694; 435/254.2; 435/325; 435/364; 435/367; 435/360; 435/354; 435/357; 435/355
[58] Field of Search ............... 435/69.4, 240.2, 435/254.2, 320.1

[56] References Cited

FOREIGN PATENT DOCUMENTS

| 0386752 | 9/1990 | European Pat. Off. ........ C12N 15/18 |
| 91/03569 | 3/1991 | WIPO ................ C12Q 1/00 |

OTHER PUBLICATIONS

Ullrich et al., "Human B–nerve growth factor gene sequence highly homologous to that of mouse" *Nature*, vol. 30, 1983 pp. 821–825.

Kaisho et al., "Cloning and expression of a cDNA encoding a novel human neurotrophic factor" *FEBS Letters*, vol. 266, 1990 pp. 187–191.

Hohn et al., "Identification and Characterization of a novel member of the nerve growth factor/brain–derived neurotrophic factor family" *Nature*, vol. 344, 1990, pp. 339–341.

Maisonpierre et al. "Neurothrophin–3: A neurotrophic Factor Related to NGF and BDNF" *Science*, vol. 247 (1990) pp. 1446–1451.

Rosenthal et al. "Primary Structure and Biological Activity of a Novel Human Neutotrophic Factor" *Neuron* vol. 4 (1990) pp. 767–773.

Ernfors et al., "Molecular cloning and neurotrophic activities of a protein with structural similarities to nerve growth factor" *Proc. Nat'l. Acad. Sci. USA*, vol. 87, (1990) pp. 5454–5458.

Jones et al., "Molecular cloning of a human gene that is a member of the nerve growth factor family" *Proc. Nat'l. Acad. Sci. USA*, vol. 87, (1990) pp. 8060–8064.

Sambrook et al. (1989), Molecular Cloning: A Laboratory Manual, 2nd ed. (Cold Spring Harbor Press, Cold Spring Harbor, N.Y.), pp. 16.30–16.36.

*Primary Examiner*—Mindy Fleisher
*Assistant Examiner*—Nancy J. Degen
*Attorney, Agent, or Firm*—David G. Conlin; David S. Resnick; Dike, Bronstein, Roberts & Cushman

[57] ABSTRACT

A transformant, which harbors a recombinant vector containing a DNA which codes for human nerve growth factor 2 and a DNA which codes for the pro-region of a nerve growth factor at 5'-terminal of said DNA, produces human nerve factor 2 in stable and large amount in a culture medium.

9 Claims, 14 Drawing Sheets

FIG. 7A

```
GAATTCGGCC ATG TCC ATC TTG TTT TAT GTG ATA TTT CTC GCT TAT CTC                              49
           Met Ser Ile Leu Phe Tyr Val Ile Phe Leu Ala Tyr Leu
           └→signal CGT GGC ATC CAA GGT AAC AAC ATG GAT CAA AGG AGT TTG CCA GAA GAC                             97
Arg Gly Ile Gln Gly Asn Asn Met Asp Gln Arg Ser Leu Pro Glu Asp
-125                          └→pro TCG CTC AAT TCC CTC ATT AAG CTG ATC CAG GCA GAT ATT TTG AAA                                145
Ser Leu Asn Ser Leu Ile Lys Leu Ile Gln Ala Asp Ile Leu Lys AAC AAG CTC TCC AAG CAG ATG GTG GAC GTT AAG GAA AAT TAC CAG AGC                            193
Asn Lys Leu Ser Lys Gln Met Val Asp Val Lys Glu Asn Tyr Gln Ser ACC CTG CCC AAA GCT GAG GCT CCC CGA GAG CCG GAG CGG GGA GGG CCC                            241
Thr Leu Pro Lys Ala Glu Ala Pro Arg Glu Pro Glu Arg Gly Gly Pro GCC AAG TCA GCA TTC CAG CCA GTG ATT GCA ATG GAC ACC GAA CTG CTG                            289
Ala Lys Ser Ala Phe Gln Pro Val Ile Ala Met Asp Thr Glu Leu Leu CGA CAA CAG AGA CGC TAC AAC TCA CCG CGG GTC CTG TAT CTC AGC GAC AGC                        337
Arg Gln Gln Arg Arg Tyr Asn Ser Pro Arg Val Leu Tyr Leu Ser Asp Ser ACC CCC TTG GAG CCC CCG CCC TTG TAT CTC ATG GAG GAT TAC GTG GGC                            385
Thr Pro Leu Glu Pro Pro Pro Leu Tyr Leu Met Glu Asp Tyr Val Gly AGC CCC GTG GTG GCG AAC AGA ACA TCA CGG CGG AAA CGG TAC GCG GAG                            433
Ser Pro Val Val Ala Asn Arg Thr Ser Arg Arg Lys Arg Tyr Ala Glu
                                                    └→mature
```

```
CAT AAG AGT CAC CGA GGG GAG TAC TCG GTA TGT GAC AGT GAG AGT CTG    481
His Lys Ser His Arg Gly Glu Tyr Ser Val Cys Asp Ser Glu Ser Leu

TGG GTG ACC GAC AAG TCA TCG GCC ATC GAC ATT CGG GGA CAC CAG GTC    529
Trp Val Thr Asp Lys Ser Ser Ala Ile Asp Ile Arg Gly His Gln Val

ACG GTG CTG GGG GAG ATC AAA ACG GGC AAC TCT CCC GTC AAA CAA TAT    577
Thr Val Leu Gly Glu Ile Lys Thr Gly Asn Ser Pro Val Lys Gln Tyr

TTT TAT GAA ACG CGA TGT AAG GAA GCC AGG CCG GTC AAA AAC GGT TGC    625
Phe Tyr Glu Thr Arg Cys Lys Glu Ala Arg Pro Val Lys Asn Gly Cys

AGG GGT ATT GAT GAT AAA CAC TGG AAC TCT CAG TGC AAA ACA TCC CAA    673
Arg Gly Ile Asp Asp Lys His Trp Asn Ser Gln Cys Lys Thr Ser Gln

ACC TAC GTC CGA GCA CTG ACT TCA GAG AAC AAT AAA CTC GTG GGC TGG    721
Thr Tyr Val Arg Ala Leu Thr Ser Glu Asn Asn Lys Leu Val Gly Trp

CGG TGG ATA CGG ATA GAC ACG TCC TGT GTG TGT GCC TTG TCG AGA AAA    769
Arg Trp Ile Arg Ile Asp Thr Ser Cys Val Cys Ala Leu Ser Arg Lys

ATC GGA AGA ACA TGAATTGGCA TCTCTCCCCA TATATAAATT ATTACTTTAA        821
Ile Gly Arg Thr

ATTATATGAT ATGCATGTAG CATATAAATG TTTATATTGT TTTTATATAT TATAAGTTGA  881

CCTTTATTTA TTAAACTTCA GCAACCCTAC AGTATATAGG CTTTTTTCTC AATAAAATCA  941

GTGTGCTTGC CTTCCCTCAG GCAGATCT                                    969
```

FIG.7B

```
TAGCTTGCCG CCACC ATG TCC ATG TTG TTC TAC ACT CTG ATC ACA GCT TTT        51
                 Met Ser Met Leu Phe Tyr Thr Leu Ile Thr Ala Phe
                 └→signal CTG ATC GGC ATA CAG GCG GAA CCA CAC TCA GAG AGC AAT GTC CCT GCA        99
Leu Ile Gly Ile Gln Ala Glu Pro His Ser Glu Ser Asn Val Pro Ala
                            └→pro GGA CAC ACC ATC CCC CAA GTC CAC TGG ACT AAA CTT CAG CAT TCC CTT       147
Gly His Thr Ile Pro Gln Val His Trp Thr Lys Leu Gln His Ser Leu GAC ACT GCC CTT CGC AGA GCC CGC AGC GCC CCG GCA GCG GCG ATA GCT       195
Asp Thr Ala Leu Arg Arg Ala Arg Ser Ala Pro Ala Ala Ala Ile Ala GCA CGC GTG GCG GGG CAG ACC CGC AAC ATT ACT GTG GAC CCC AGG CTG       243
Ala Arg Val Ala Gly Gln Thr Arg Asn Ile Thr Val Asp Pro Arg Leu TTT AAA AAG CGG CGA CTC CGT TCA CCC CGT GTG CTG TTT AGC ACC CAG       291
Phe Lys Lys Arg Arg Leu Arg Ser Pro Arg Val Leu Phe Ser Thr Gln CCT CCC CGT GAA GCT GCA GAC ACT CAG GAT CTG GAC TTC GAG GTC GGT       339
Pro Pro Arg Glu Ala Ala Asp Thr Gln Asp Leu Asp Phe Glu Val Gly GGT GCT GCC CCC TTC AAC AGG ACT CAC AGG AGC AAG CGC TAC GCG GAG       387
Gly Ala Ala Pro Phe Asn Arg Thr His Arg Ser Lys Arg Tyr Ala Glu
                                                        └→mature CAT AAG AGT CAC CGA GGG GAG TAC TCG GTA TGT GAC AGT GAG AGT CTG       435
His Lys Ser His Arg Gly Glu Tyr Ser Val Cys Asp Ser Glu Ser Leu
```

```
TGG GTG ACC GAC AAG TCA TCG GCC ATC GAC ATT CGG GGA CAC CAG GTC    483
Trp Val Thr Asp Lys Ser Ala Ile Asp Ile Arg Gly His Gln Val

ACG GTG CTG GGG GAG ATC AAA ACG GGC AAC TCT CCC GTC AAA CAA TAT    531
Thr Val Leu Gly Glu Ile Lys Thr Gly Asn Ser Pro Val Lys Gln Tyr

TTT TAT GAA ACG CGA TGT AAG GAA GCC AGG CCG GTC AAA AAC GGT TGC    579
Phe Tyr Glu Thr Arg Cys Lys Glu Ala Arg Pro Val Lys Asn Gly Cys

AGG GGT ATT GAT GAT AAA CAC TGG AAC TCT CAG TGC AAA ACA TCC CAA    627
Arg Gly Ile Asp Asp Lys His Trp Asn Ser Gln Cys Lys Thr Ser Gln

ACC TAC GTC CGA GCA CTG ACT TCA GAG AAC AAT AAA CTC GTG GGC TGG    675
Thr Tyr Val Arg Ala Leu Thr Ser Glu Asn Asn Lys Leu Val Gly Trp

CGG TGG ATA CGG ATA GAC ACG TCC TGT GTG TGT GCC TTG TCG AGA AAA    723
Arg Trp Ile Arg Ile Asp Thr Ser Cys Val Cys Ala Leu Ser Arg Lys
                                                              115

ATC GGA AGA ACA TGAATTGGCA TCTCTCCCCA TATATAAATT ATTACTTTAA        775
Ile Gly Arg Thr

ATTATATGAT ATGCATGTAG CATATAAATG TTTATATATT TTTATATAT TATAAGTTGA   835

CCTTTATTTA TTAAACTTCA GCAACCCTAC AGTATATAGG CTTTTTTCTC AATAAAATCA  895

GTGTGCTTGC CTTCCCTCAG GCAGATCT                                    923
```

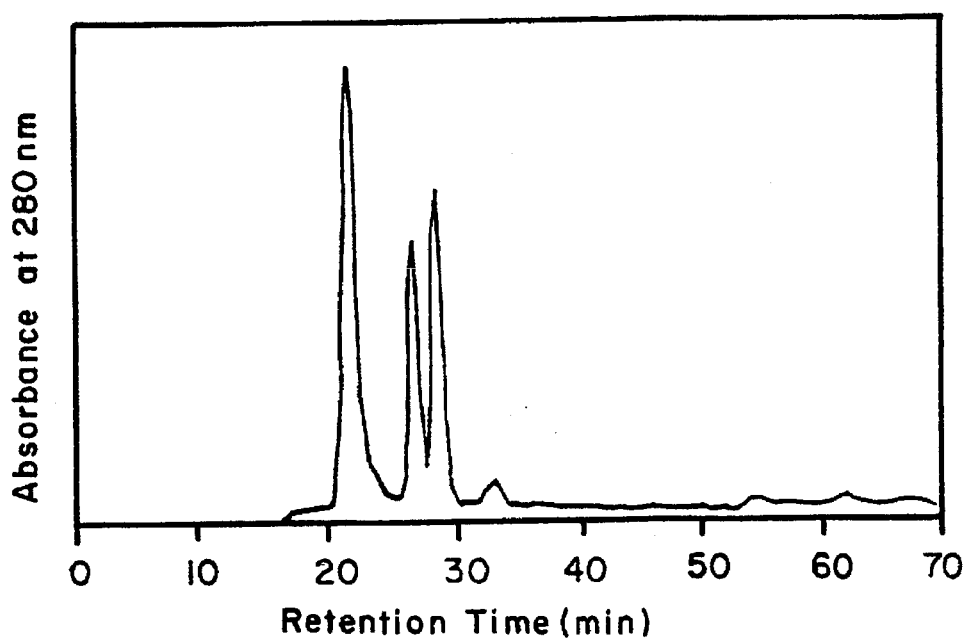
FIG. 19
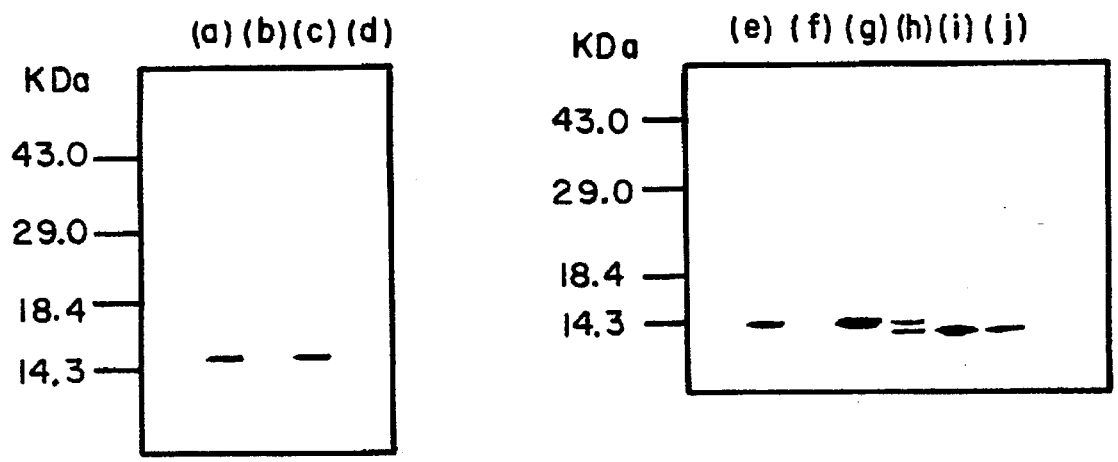
FIG. 20A
FIG. 20B

METHOD FOR PRODUCING HUMAN NERVE GROWTH FACTOR 2

This is a continuation of application Ser. No. 08/154,697 filed on Nov. 18, 1993, abandoned, which is a continuation of Ser. No. 07/834,676 filed on Feb. 12, 1992, also abandoned.

FIELD OF INVENTION

The present invention relates to a recombinant DNA technology for producing human nerve growth factor 2 (hereinafter also referred to as human NGF2/NT-3).

BACKGROUND OF THE INVENTION

Since the discovery of nerve growth factor (NGF) by Levi-Monntalcini (Annual New York Academy of Science, 55, 330 (1952)) and Cohen et al. (Proceedings of National Academy of Science, USA, 40, 1014 (1954)), a large number of neurotrophic factors have been found. These factors are believed to play various roles such as nerve cell differentiation, maturation, survival, homeostasis and proliferation. In addition to the above-mentioned NGF, these factors include brain-derived neurotrophic factor (BDNF) (Barde Y-A et al., EMBO J. 1, 549–553 (1982)) and ciliary neurotrophic factor (CNTF) (Watters, D. et al, J. Neurochem., 49, 705–713 (1987)). Neurotrophic activity is also found in fibroblast growth factors (FGFS), epidermal growth factor (EGF), insulin-like growth factor (IGF) and interleukin-6 (IL-6).

As a factor showing high homology to NGF, human nerve growth factor 2 was discovered by Kaisho et al. (European Patent Publication No. 386,752; FEBS Letters, 266, 187–191 (1990)).

The same factor has been reported in other publications (e.g., Hohn et al., Nature, 344, 399 (1990)).

In the present specification, human nerve growth factor 2 is also referred to as human NGF2/NT-8. With respect to its human NGF2/NT-3, while much remains unknown as to action and structure, the following is known: (1) The human NGF2/NT-3 gene is highly expressed in the human hippocampus and cerebellum. (2) The degree of expression is higher in newborns than mature animals (rats). (3) It acts on nerve cells on which NGF or BDNF has no or weak action, such as nodose ganglion derived nerve cells. These findings suggest that human NGF2/NT-3 plays a key role in nervous system development.

Production of human NGF2/NT-3 in large amounts will help to further elucidate its bioactivities, which in turn, will facilitate commercial production thereof.

BRIEF DESCRIPTION OF THE DRAWINGS

FIG. 7 (SEQ ID NO: 6) shows the sequence of the DNA which codes for the pro-region of NGF2/NT-3, the DNA which codes for NGF2/NT-3 and the vicinity DNA present on the plasmid pTB1339 obtained in Reference Example 4.

FIG. 8 (SEQ ID NO: 9) shows the sequence of the DNA which codes for the pro-region of NGF, DNA which codes for NGF2/NT-3 and vicinity DNA present on the plasmid pTB1344 obtained in Example 1.

FIG. 19 shows the the results of the chromatography using reversed phase HPLC obtained in Example 10.

FIG. 20(A) shows the SDS-PAGE results and FIG. 20(B) shows the results of Western blotting obtained in Example 10.

SUMMARY OF THE INVENTION

Figure 1:
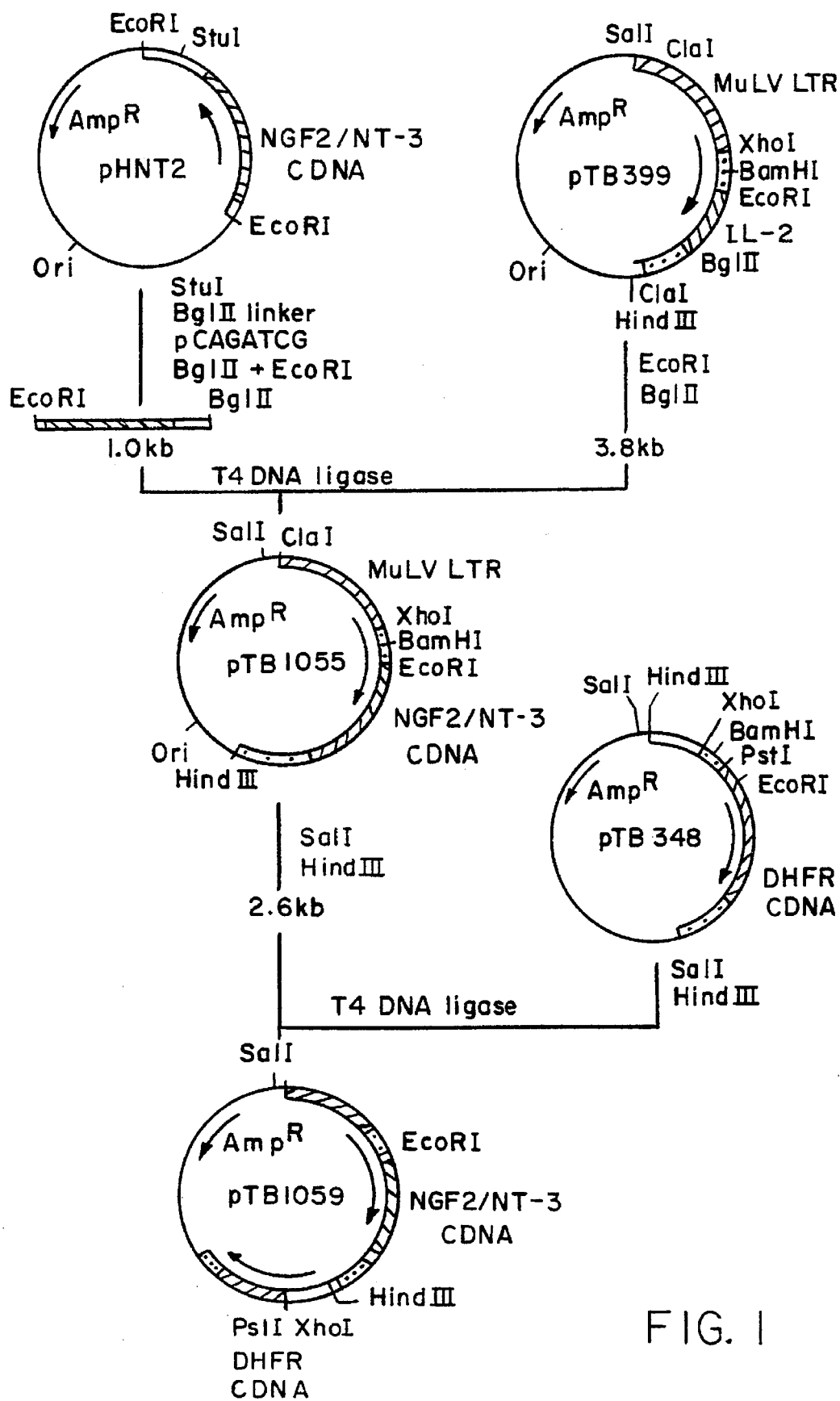
FIG. 1 diagrams the construction of the plasmid pTB1056 obtained in Example 1.

The present inventors have found that human NGF2/NT-3 can be expressed stably in large amounts by the use of a vector constructed whereby a DNA which codes for the pro-region of nerve growth factor is introduced on the 5'-terminal side of a DNA which codes for human NGF2/NT-3. Based on this finding the present invention was completed.

Thus, the present invention is directed to a vector comprising a DNA coding for a pro-region of nerve growth factor and a DNA coding for human NGF2/NT-3, and its use.

In accordance with the present inention, there is provided (1) a recombinant vector containing a DNA having a DNA which codes for human nerve growth factor 2 and a DNA which codes for the pro-region of a nerve growth factor at 5'-terminal of the DNA which codes for human nerve growth factor 2, (2) a transformant transformed with the vector described in (1) above, and (3) a method for producing human nerve growth factor 2, which comprises cultivating the transformant described in (2) above in a culture medium.

DETAILED DESCRIPTION OF THE INVENTION

The recombinant human NGF2/NT-3 obtained by the present invention may comprise the 119 amino acid residues indicated as "mature" in FIG. 7 and may have additional methionine at the N-terminal location. The human NGF2/NT-3 of the present invention may also be a mutein lacking 1 to 5 residues at the N-terminal location of human NGF2/NT-3. Preferably the mutein of human NGF2/NT-3 is a molecule which lacks 5 residues from the N-terminal location of human NGF2/NT-3 and comprises 114 amino acid residues.

The human NGF2/NT-3 gene used for the present invention can be obtained by cloning from a human genome library, by cloning from a human cDNA library, by the polymerase chain reaction (PCR) method from a human genome DNA, mRNA or cDNA, and by chemical synthesis. Cloning of the human NGF2/NT-3 gene can, for example, be achieved by the method described in Neuron, 4, 767-773 (1990).

Said gene is exemplified in European Patent Publication No. 386,752; Maisonpierre, P. C. et al., Science, 247, 1446-1451 (1990); Rosenthal, A. et al., Neuron, 4, 767-773 (1990); Ernfors, P. et al., Proc. Natl. Acad. Sci., USA, 87, 5454-5458 (1990) and Kaisho, Y. et al., FEBS Lett., 266, 187-191 (1990).

In the present invention, a DNA which codes for the pro-region of NGF is connected to the 5'-terminal of a DNA which codes for human NGF2/NT-3, as described above. In preferred embodiment of the present invention, a DNA which codes for signal peptide is ligated upstream of the pro-region of NGF. When the gene is expressed in an animal cell, any signal peptide can be used, as long as it allows secretion of human NGF2/NT-3. Examples of such signal peptides include those for the NGF2/NT-3 of rats, mice and other animals, the signal peptides for mouse, swine, human and rat BDNF and human, rat, mouse, bovine and arian NGF, the signal peptide for albumen lysozyme and variants thereof, and the signal peptide for human interleukin-2.

In addition to the method described above, human NGF2/NT-3 can also be obtained by causing the host to produce and secrete a fused protein comprising human NGF2/NT-3 and another protein and then carrying out cleavage using an appropriate protease.

The DNA which codes for human NGF2/NT-3 described above etc. is used to construct a human NGF2/NT-3 expression vector.

Examples of expression hosts include animal cells and yeasts.

Examples of the pro-region of NGF include the pro-regions of human NGF, mouse NGF, bovine NGF, arian NGF, rat NGF and snake NGF. DNAs which code for these pro-regions can be obtained by cloning from an animal genome DNA library or cDNA library, and can also be obtained by chemical synthesis based on the amino acid sequences thereof. The pro-region of NGF may be a variant resulting from, for example, partial insertion, addition, deletion, substitution etc. of amino acids within the amino acid sequence of the pro-region of NGF.

Pro-region examples include the pro-region of human NGF gene described by Ullrich, A. et al. in Nature, 303, 821-825 (1983), the pro-region of rat NGF gene described by Whittemore, S. R. et al. in J. Neurosci. Res., 20, 403-410 (1988), the pro-region of mouse NGF gene described by Scott, J. et al. in Nature, 302, 538-540 (1983), and the pro-regions of bovine and arian NGF described by Meier, R. et al. in EMBO J., 5, 1489-1493 (1986).

The pro-region is preferably the pro-region of human NGF.

When human NGF2/NT-3 is expressed in an animal cell, examples of the vector used to construct an expression vector include pBR322 and derivatives thereof, SV40 vector, bovine papilloma virus vector, retrovirus vector and BK virus vector. Also usable are animal viruses such as EB virus and herpes simplex virus.

Any promoter can be used for the expression vector in an animal cell, as long as it functions in the animal cell selected. Examples of such promoters include the SV40 promoter, LTR promoter, metallothionein promoter and cytomegalovirus promoter.

In addition to the promoter, the expression vector preferably incorporates an enhancer, an RNA splicing signal, a poly-A addition signal and a selection marker.

An expression vector can be constructed by a known method, including the method described in Molecular Cloning, A Laboratory Manual, Cold Spring Harbor Laboratory (1982).

The human NGF2/NT-3 expression vector thus prepared is used to transform animal cells to yield transformants.

Examples of animal cells used for the present invention include simian Vero cells, human Hela cells, Chinese hamster CHO cells, mouse L cells, mouse C127 cells, mouse BALB/3T3 cells, and lymphocytes such as mouse Sp2/0, rat NRK cells and simian CV-1 cells, with preference given to Chinese hamster CHO cells.

Animal cells can be transformed by a known method, including the method of Graham (Virology, 52, 456 (1973)).

Animal cells transformed with human NGF2/NT-3 expression vector are thus obtained.

Preferred methods for stably expressing the human NGF2/NT-3 gene using an animal cell transformed with a human NGF2/NT-3 expression vector in accordance with the present invention include a method in which the NGF2/NT-3 expression vector is incorporated into a chromosome of the host cell and a method in which the NGF expression vector is kept stable in the host cell without being incorporated in the chromosome thereof. The former makes it possible to increase the productivity for human NGF2/NT-3 using an amplification system such as the dihydrofolate reductase (DHFR) gene (Journal of Molecular Biology, 159, 601 (1982)).

Transformed animal cells (clones) can be selected by a known method, including the method described in Jikken Igaku (Experimental Medicine), extra issue, vol. 5, No. 11 (1987). Specifically, transformants are selected using a selection marker gene as an indicator along with the human NGF2/NT-3 gene. In this case, the selection marker may be introduced in the cell on a single vector along with the human NGF2/NT-3 gene, or along with an excess of the human NGF2/NT-3 gene on a separate vector (co-transformation). Examples of such selection markers include dihydrofolate reductase (DHFR) (methotrexate (MTX) resistance), thymidine kinase, Ecogpt gene (mycophenolic acid resistance), neogene (G418 resistance) and hygromycin B phosphotransferase gene (hygromycin B resistance).

Examples of medium for cultivating the animal cells thus obtained include MEM medium containing about 0.5 to about 20% fetal bovine sexism (Science, 122, 501 (1952)), DMEM medium (Virology, 8, 396 (1959)), RPMI 1640 medium (Journal of American Medical Association, 199, 519 (1967)) and 199 medium (Proceedings of the Society of Experimental Biological Medicine, 73, 1 (1950)). The optimal medium pH is 6 to 8. Cultivation is normally carried out at about 30° to 40° C. for 1 to 10 days, with aeration and/or stirring as necessary.

Signal peptides for expression in yeasts are exemplified by the same signal peptides for expression in animal cells as above. Other examples include the signal sequence for human lysozyme, the signal sequence for albumen lysozyme, variants (modified signal sequences) of the signal sequence for albumen lysozyme, the signal sequences for *Saccharomyces cerevisiae* α-factor, phosphatase, invertase and killer factor, and the signal sequence for *Aspergillus awamori* glucoamylase.

A DNA which codes for the signal sequence-NGF pro-region-human NGF described above may also be used to construct a human NGF expression vector for yeasts.

Any vector can be used to construct a human NGF expression vector, as long as it functions in yeasts. Examples of such vectors include pSH19, pSH15, pSH32 and derivatives thereof.

Any promoter can be used for the expression vector, as long as it functions in yeasts. Examples of such promoters include the GLD promoter, α-factor promoter, GAL10 promoter, GAL1 promoter, PH05 promoter and PGK promoter.

In preferred embodiments, expression efficiency is increased by inserting a terminator downstream from DNA which codes for human NGF. Examples of such terminators include the PGK terminator.

As with animal cells, an expression vector can be constructed by a known method, including the method described in Molecular Cloning, A Laboratory Manual, Cold Spring Harbor Laboratory (1982).

The human NGF expression vector thus prepared is used to transform a yeast to yield a transformant.

Examples of yeasts include *Saccharomyces cerevisiae* AH22R⁻, *S. cerevisiae* NA74-3Ap⁻, *S. cerevisiae* TB39p⁻ and variants thereof.

Transformation can be achieved by any known method, such as the lithium method (Ito et al., Journal of Bacteriology, 153, 163 (1983)) and the protoplast method (Hinnen et al., Proceedings of the National Academy of Science, USA, 75, 1927 (1978)).

The transformant thus obtained is cultivated by any known method.

Examples of culture medium include Burkholder's minimal medium (American Journal of Botany, 30, 206 (1943)) and modifications thereof (Tohe, A. et al., Journal of Bacteriology, 113, 727 (1973)). Usually cultivation is carried out between about 15° to 40° C., preferably between about 24° to 30° C. for 10 to 168 hours, preferably 48 to 96 hours. Although both shaking and standing culture are possible, aeration and/or stirring is employed as necessary.

The human NGF2/NT-3 of the present invention is produced and accumulated intracellularly or extracellularly. For extracting intracellular human NGF2/NT-3 from the culture, several methods are available, such as collecting cultured cells by a known method and suspension in a buffer containing a protein denaturant such as guanidine hydrochloride or urea or in a buffer containing a surfactant such as Triton X-100, followed by centrifugation to yield a supernatant containing human NGF2/NT-3, and a method of disrupting cells by ultrasonic treatment or freeze-thawing, followed by centrifugation to yield a supernatant containing human NGF.

For separating and purifying the human NGF2/NT-3 produced and accumulated in these supernatants or extracellularly, known methods of separation and purification can be performed in combination as appropriate. Examples of known methods of separation and purification include those based on differences in solubility such as salting-out and solvent precipitation, methods based on differences in molecular weight such as dialysis, ultrafiltration and SDS-polyacrylamide gel electrophoresis, methods based on differences in charge such as ion exchange chromatography, methods based on specific affinity such as affinity chromatography, methods based on differences in hydrophobicity such as reverse phase high performance liquid chromatography (HPLC) and methods based on different isoelectric points such as isoelectric focusing.

An active product with a purity of over 90% (w/w) is thus obtained. The purity is determined by HPLC, SDS-PAGE and bioassay.

Preferred methods of bioassay include using nurite elongation of the avian embryonic vertebral dorsal root ganglion as an index (Saibo Seicho Inshi (Growth Factors), edited by the Japanese Tissue Culture Association, Asakura Shoten (1984)).

The human NGF2/NT-3 thus obtained may be used as a reagent for research on the brain and nervous system and is expected to serve as a therapeutic drug for senile dementia.

For using human NGF2/NT-3 for such research, it is preferable to add human NGF2/NT-3 at about 0.1 to 1,000 ng, more preferably about 1 to 100 ng per ml of animal cell culture medium.

Use of the vectors of the present inventions makes it possible to produce human NGF2/NT-3 stably and in large amount. Therefore, the present invention provides for industrial large scale production of human NGF2/NT-3.

Abbreviations for bases and amino acids used in the present specification and drawings attached thereto are based on abbreviations specified by the IUPAC-IUB Commission on Biochemical Nomenclature or abbreviations in common use in relevant fields. Some examples are given below. When there is a possibility of the presence of an optical isomer in an amino acid, it is of the L-configuration, unless otherwise stated.

DNA: Deoxyribonucleic acid
A: Adenine
C: Cytosine
G: Guanine
T: Thymine
Ala: Alanine
Arg: Arginine
Asn: Asparagine
Asp: Aspartic acid
Cys: Cysteine
Gln: Glutamine
Glu: Glutamic acid
Gly: Glycine
His: Histidine
Ile: Isoleucine
Leu: Leucine
Lys: Lysine
Met: Methionine
Phe: Phenylalanine
Pro: Proline
Ser: Serine
Thr: Threonine
Trp: Tryptophan
Tyr: Tyrosine
Val: Valine The transformant CHO-N2-1 obtained in Example 4 below has been deposited under accession number IFO 50307 at the Institute for Fermentation, Osaka (IFO), Japan since Jan. 22, 1991, and has been deposited under accession number FERM BP-3255 under the Budapest Treaty at the Fermentation Research Institute, Agency of Industrial Science and Technology, Ministry of International Trade and Industry (FRI), Japan since Jan. 29, 1991.

The present invention is hereinafter described in more detail by means of the following reference examples and working examples, but the invention is not by any means limited to them.

REFERENCE EXAMPLE 1

Construction of human NGF expression vector (1)

A λEMBL 3 genome library prepared from human leukocyte DNA (Clontech Laboratories Inc.) was infected with

*Escherichia coli* NM538, after which its clones were spread over soft agar plates at about $3 \times 10^4$ clones per plate. After transferring the plaque to a nylon membrane (Hibond-N, produced by Amersham Corporation), the nylon membrane was immersed in a solution of 0.5N NaOH and 1.5M NaCl for 6 minutes to denature the phage DNA and then immersed in a solution of 0.5M Tris-HCl (pH 8.0) and 1.5M NaCl for 6 minutes. The membrane was immersed in a 2×SSC solution and air dried, after which it was heated at 80° C. for 2 hours to immobilize the DNA thereon.

Separately, a DNA (0.38 kb) which codes for human β-NGF was chemically synthesized in accordance with a known human NGF gene (Ullrich, A. et al., Nature, 303, 821 (1983)) and labeled with asp using a DNA labeling kit (Nippon Gene) to yield a probe.

The DNA-immobilized filter was incubated in 10 ml of a solution containing the labeled probe, 6×SSC (1×SSC= 0.15M NaCl, 0.015M sodium citrate), 5×Denhardt's solution, 0.5% SDS and 20 µg/ml denatured salmon spermatic DNA at 65° C. for 16 hours. After reaction, the filter was washed in a solution containing 2×SSC and 0.1% SDS at room temperature in three 5-minute cycles and then in a solution containing 1×SSC and 0.1% SDS at 60° C. for 60 minutes. After drying the washed filter, a radioautogram was taken to search the clone which reacts with the probe. From the clone λβLN2113 thus obtained, a phage DNA was extracted by the method of Davis et al. (Advanced Bacterial Genetics, Cold Spring Harbor Laboratory (1980)).

Then, λβLN2113 was cleaved with Sma I and Apa I to cleave out a DNA (about 1 kb) containing the human NGF gene, which was inserted to plasmid pBluescript II KS- (Stratagene, USA) between the Sma I and Apa I sites to yield the plasmid pNGFP107G.

Also, the same fragment was inserted into pBluescript II KS-(Stratagene) between the Sma I and Apa I sites to yield pNGFP1086. The base sequence of the fragment inserted in pNGFP1076 and pNGFP1086 was determined using Sequenase (United States Biochemical Corporation). The base sequence thus determined was identical with the sequence described in Nature, 303, 821 (1983) in the protein encoding region.

The above phage λβLN2113 DNA was cleaved with restriction enzyme Bgl II to isolate a DNA fragment (1.8 kb) containing the human NGF gene. Separately, pKSV-10 (Pharmacia), an expression vector for animal cells, was cleaved with restriction enzyme Bgl II; the resulting fragment was ligated with the DNA fragment (1.8 kb) containing the human NGF gene using T4 DNA ligase. Using this reaction mixture, *Escherichia coli* DH1 was transformed to yield ampicillin-resistant transformants, from one (*Escherichia coli* DH1/pMNGF101) of which a plasmid was isolated and named pMNGF101.

REFERENCE EXAMPLE 2

Construction of human NGF expression vector (2)

The plasmid pNGFP107G obtained in Reference Example 1 was cleaved with restriction enzymes Bcl I and Apa I to isolate a DNA fragment (0.8 kb) containing the human NGF gene. This 0.8 kb Bcl I-Apa I fragment was mixed with chemically synthesized adapters SN1, SN2 and SN3 and ligated using T4 DNA ligase, after which it was cleaved with Bgl II to yield a 0.8 kb Hind III-Bgl II DNA fragment.

| | |
|---|---|
| SN1: | 5'-AGCTTGCCGCCACCATGTCCATGTTGTTCTACACTCT-3' (SEQ ID NO: 1) (37mer) |
| SN2: | 5'-GATCAGAGTGTAGAACAACATGGACATGGTGGCGGCA-3' (SEQ ID NO: 2) (37mer) |
| SN3: | 5'-C<u>AGATCT</u>GGGCC-3' (SEQ ID NO: 3) (12 mer) BglII Apa I |

The plasmid pSV2-gpt (Science, 209, 1422 (1980)) was cleaved with restriction enzymes EcoR I and Hind II to isolate a 2.6 kb EcoR I-Hind III DNA fragment containing the SV40 promoter. Next, from the plasmid pMTVdhfr (Nature, 294, 228 (1981)) was isolated a 1.6 kb Bgl II-EcoR I fragment containing a poly-A addition region.

The above-mentioned 2.6 kb EcoR I-Hind HI DNA fragment containing the SV40 promoter, the 0.8 kb Hind HI-Bgl II DNA fragment containing the human NGF gene and the 1.6 kb Bgl II-EcoR I fragment containing a poly-A addition region were ligated using T4 DNA ligase. Using this reaction mixture, *Escherichia coli* DH1 was transformed to yield ampicillin-resistant transformants, from one (*Escherichia coli* DH1/pMNGF201) of which a plasmid was isolated and named pMNGF201.

REFERENCE EXAMPLE 3

Construction of human NGF expression vector

The plasmid pMNGF201 obtained in Reference Example 2 was cleaved with Hind III and smoothed by DNA polymerase Klenow fragment reaction, after which it was cleaved with Bgl II to isolate an about 0.8 kb DNA fragment. Separately, plasmid pTB399 (described in Japanese Patent Application Laid-open No. 63282/1986 which corresponds to European Patent Publication No. 172,619) was cleaved with EcoR I and smoothed by Klenow fragment reaction, after which it was cleaved with Bgl II to yield an about 3.9 kb DNA fragment. These two DNA fragments were cyclized by T4 DNA ligase reaction to yield the plasmid pTB1054.

REFERENCE EXAMPLE 4

Construction of human NGF2/NT-3 expression vector (1) The plasmid pHNT2 (European Patent Publication No. 386,752), which contains the human NGF2/NT-3 cDNA, was cleaved with restriction enzyme Stu I and ligated with a Bgl II linker using T4 DNA ligase. This DNA was cleaved with restriction enzymes EcoR I and Bgl II to yield a 1.0 kb DNA fragment containing the human NGF2/ NT-3 cDNA. Separately, pTB399 (Cell Struct. Funct., 12, 205 (1987), an expression plasmid for animal cells was cleaved with restriction enzymes EcoR I and Bgl II to yield an about 3.8 kb DNA fragment. These two DNA fragments were ligated using T4 DNA ligase to yield the plasmid pTB1055.

Next, pTB348 (described in Japanese Patent Appplication Laid-open No. 63282/1986 which corresponds to EP-A-172, 619), a plasmid containing the hamster dihydrofolate reductase (DHFR) cDNA, was cleaved with restriction enzymes Sal I and Hind III. This fragment was ligated with an about 2.6 kb DNA fragment obtained by cleaving the plasmid pTB1055 with restriction enzymes Sal I and Hind III to yield the plasmid pTB1059 (see FIG. 1).

Figure 2:
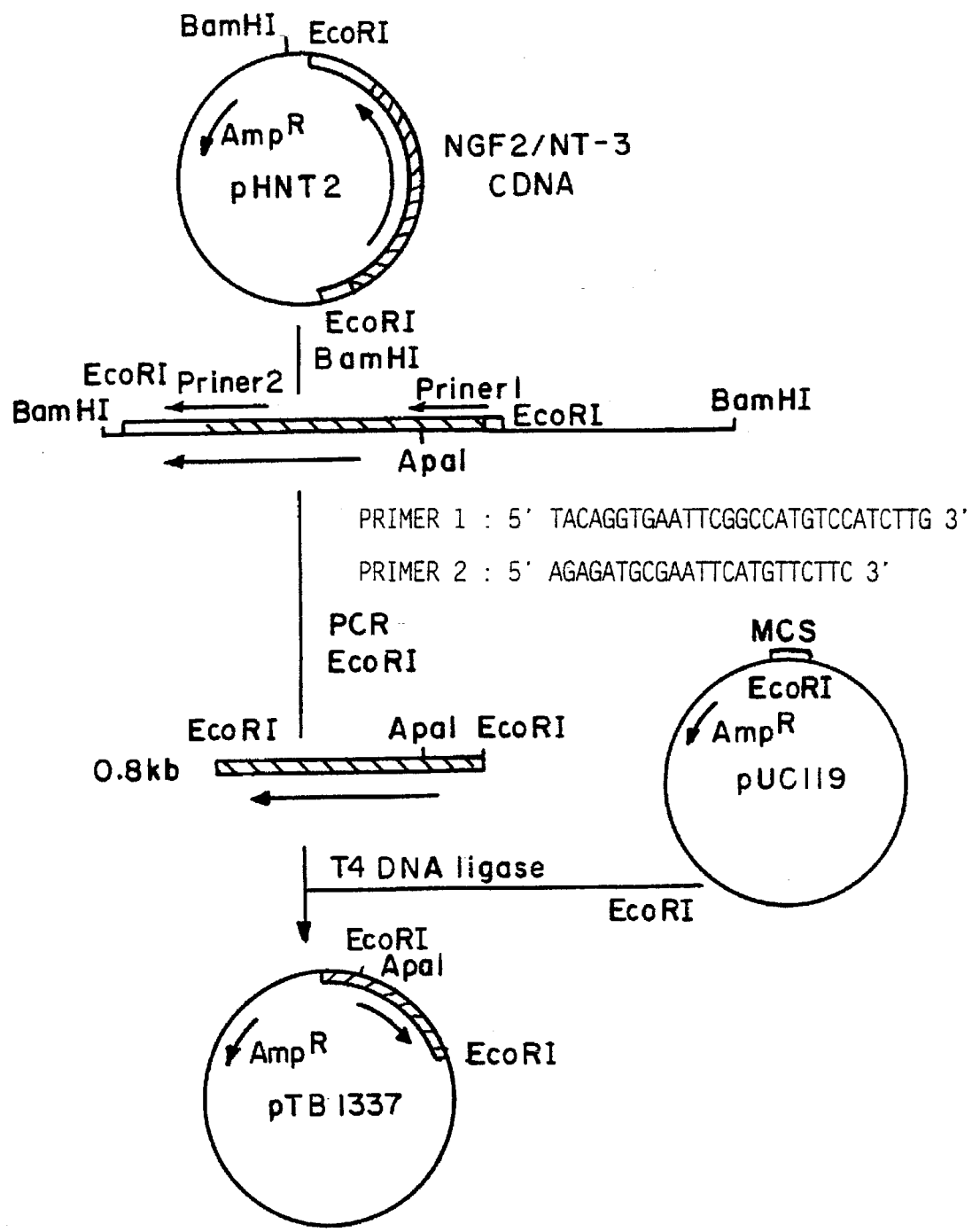
FIGS. 2 and 3 diagram the construction of the plasmid pTB1339 obtained in Example 1.

(2) The human NGF2/NT-3 gene contained in the plasmid pHNT2 described in Term (1) above has an in-frame ATG sequence upstream of its 5'-terminal (see FIG. 2 in the specification for European Patent Publication No. 386,752). For removing this ATG sequence, the following two DNA oligomers were synthesized.

Primer 1: 5'-TACAGGTGAATTCGGCCATGTCCATCTTG-3' (SEQ ID NO: 4)
Primer 2: 5'-AGAGATGCGAATTCATGTTCTTC-3' (SEQ ID NO: 5)

Figure 3:
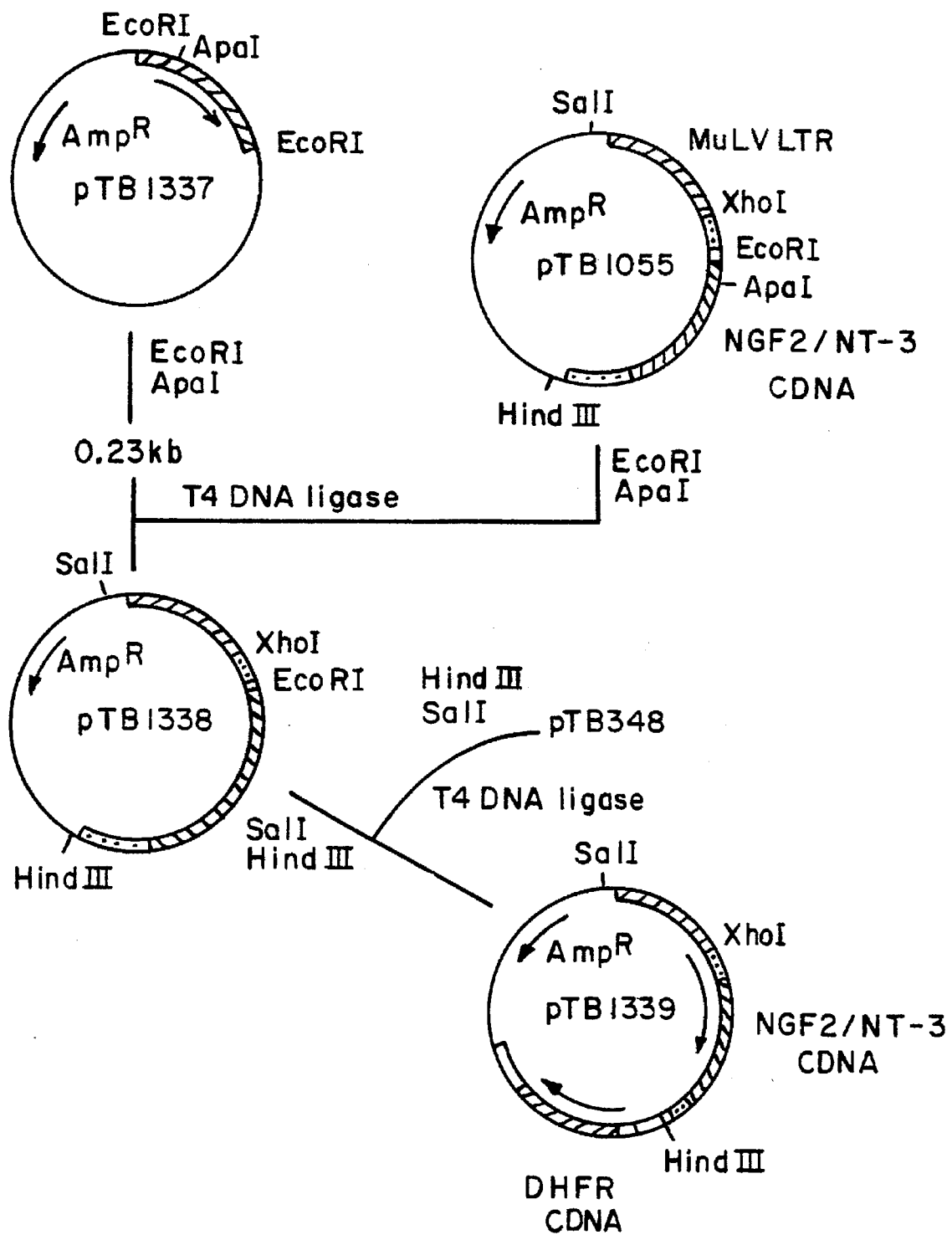

Using the primers 1 and 2, a polymerase chain reaction (PCR) was carried out as follows. The plasmid pHNT2 was cleaved with restriction enzyme BamH I, linearized and extracted with phenol, after which it was extracted with ethanol, evaporated to dryness and dissolved in distilled water. PCR was carried out in the presence of 0.3 ng of the linear pHNT2 as a template DNA and 1.0 μM of each of the primers 1 and 2 using the GeneAmp™ DNA amplification reagent kit (Perkin-Elmer Cetus, USA). Reaction was carried out in 30 cycles of 94° C. for 1 minute, 55° C. for 2 minutes and 72° C. for 3 minutes using the DNA Thermal Cycler (Perkin-Elmer Cetus). As a result, an about 0.8 kb DNA fragment was obtained. Since the primers 1 and 2 have a recognition site for restriction enzyme EcoR I, the obtained fragment was cleaved with EcoR I and subcloned to the EcoR I site of pUC119. The base sequence of the resulting recombinant primer pTB1337 was determined from the single-stranded DNA obtained by introducing it to an Escherichia coli MV1184 strain; it was found that the gene was amplified with no error in any base. This pTB1337 was cleaved out with restriction enzymes EcoR I and Apa I to yield a 0.23 kb DNA fragment. This 0.23 kb DNA was ligated with an about 4.6 kb DNA obtained by cleaving the plasmid pTB1055 described in Term (1) above with restriction enzymes EcoR I and Apa I to yield the plasmid pTB1338.

pTB1338 was cleaved with restriction enzymes Sal I and Hind III, followed by introduction of the hamster DHFR gene in the same manner as in Term (1) above to yield the expression plasmid pTB1339 (see FIGS. 2 and 3).

FIG. 7 (SEQ ID NO: 6) shows the DNA which codes for the pro-region of NGF2/NT-3, the DNA which codes for NGF2/NT-3 and the vicinity DNA on this plasmid pTB1339.

REFERENCE EXAMPLE 5

Determination of bioactivities of human NGF2/NT-3

A fertilized chicken egg was incubated at 37.5° C. for 8 to 10 days until an embryo developed. Then, the dorsal root ganglion (hereinafter referred to as DRG) was excised from the fetus. DRG was treated with a solution containing 0.125% trypsin-PBS at 37° C. for 20 minutes and pipetted to disperse the cells. This cell dispersion was suspended in a mixture of 10% fetal bovine serum, Dulbecco's modified MEM medium and 50 μg/ml kanamycin and cultivated at 37° C. in the presence of 5% $CO_2$ for 2 to 4 hours to allow the fibroblasts and other cells to adhere on the petri dish, and non-adhering cells were separated. The non-adhering cells were collected via centrifugation at 800 rpm for 5 minutes and re-suspended in a medium containing 10% fetal bovine serum, Dulbecco's modified MEM medium, Ham F-12 medium (1:1 ratio), 1 μM cytosine arabinoside (AraC, Sigma, USA) and 50 μg/ml kanamycin to a density of 10,000 cells/ml and seeded to a Polyley ornithine-coated 48-well plate at 0.5 ml/well. To this medium was added 0.5 to 20 μl of a sample solution, followed by cultivation at 37° C. in the presence of 5% $CO_2$ for 3 days, after which viable cells were counted.

EXAMPLE 1

Construction of human NGF2/NT-3 expression vector

Plasmid pHNT5 (having the same EcoR I insert as in pHNT2 but in the opposite direction) was introduced to Escherichia coli MV1183 by a conventional method to yield a (−) chain single-stranded DNA. Separately, the plasmid pNGFP1086 (see Reference Example 1) was used to prepare a human NGF (−) chain single-stranded DNA. Corresponding to these DNAs, the following were synthesized.

oligo 1: 5'-AGGAGCAAGCGCTCATCATCCCA-3' (SEQ ID NO: 8)
oligo 2: 5'-TCACGGCGGAAGCGCTACGCGGAGCAT-3' (SEQ ID NO: 7)

Figure 4:
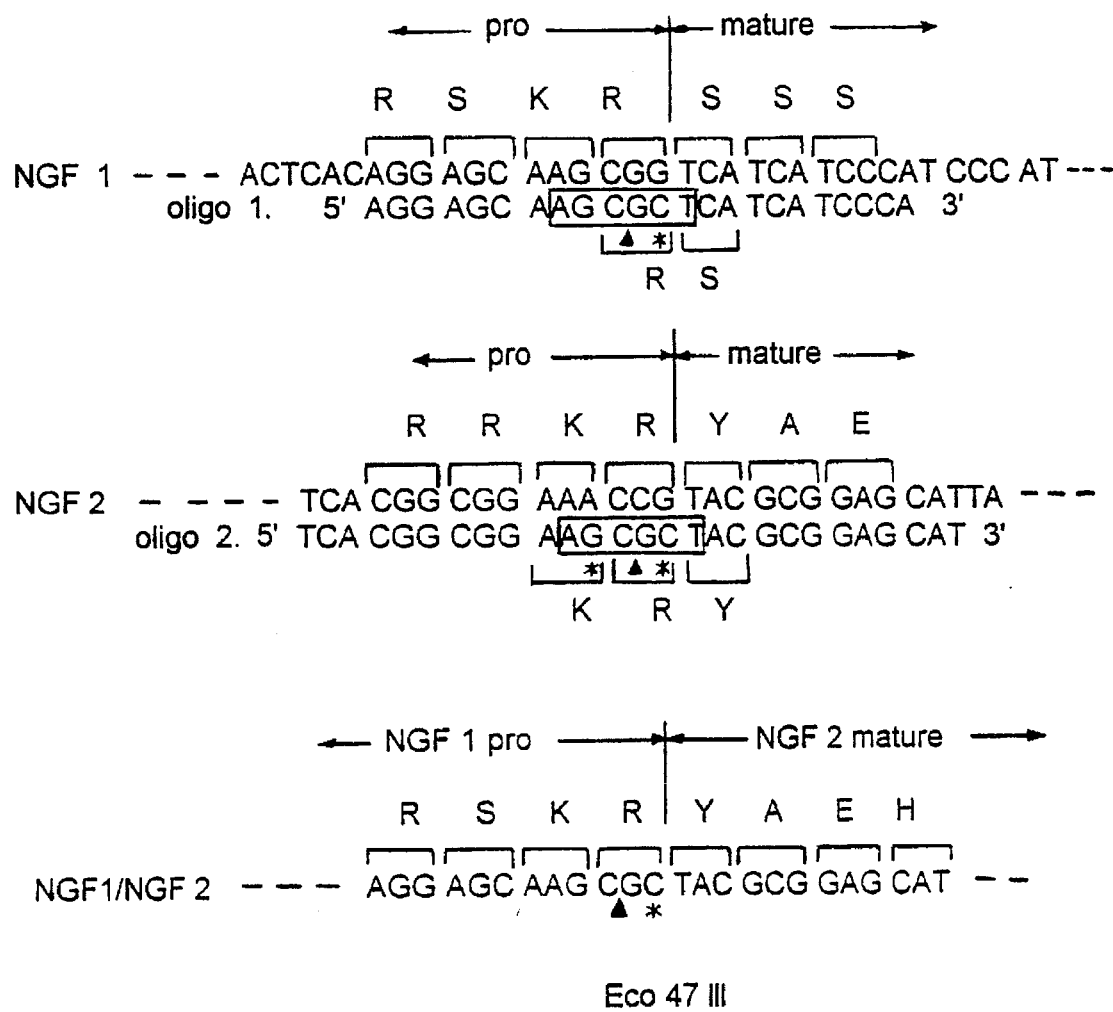
FIGS. 4, 5 and 6 diagram the construction of the plasmid pTB1344 obtained in Example 1.
Figure 5:
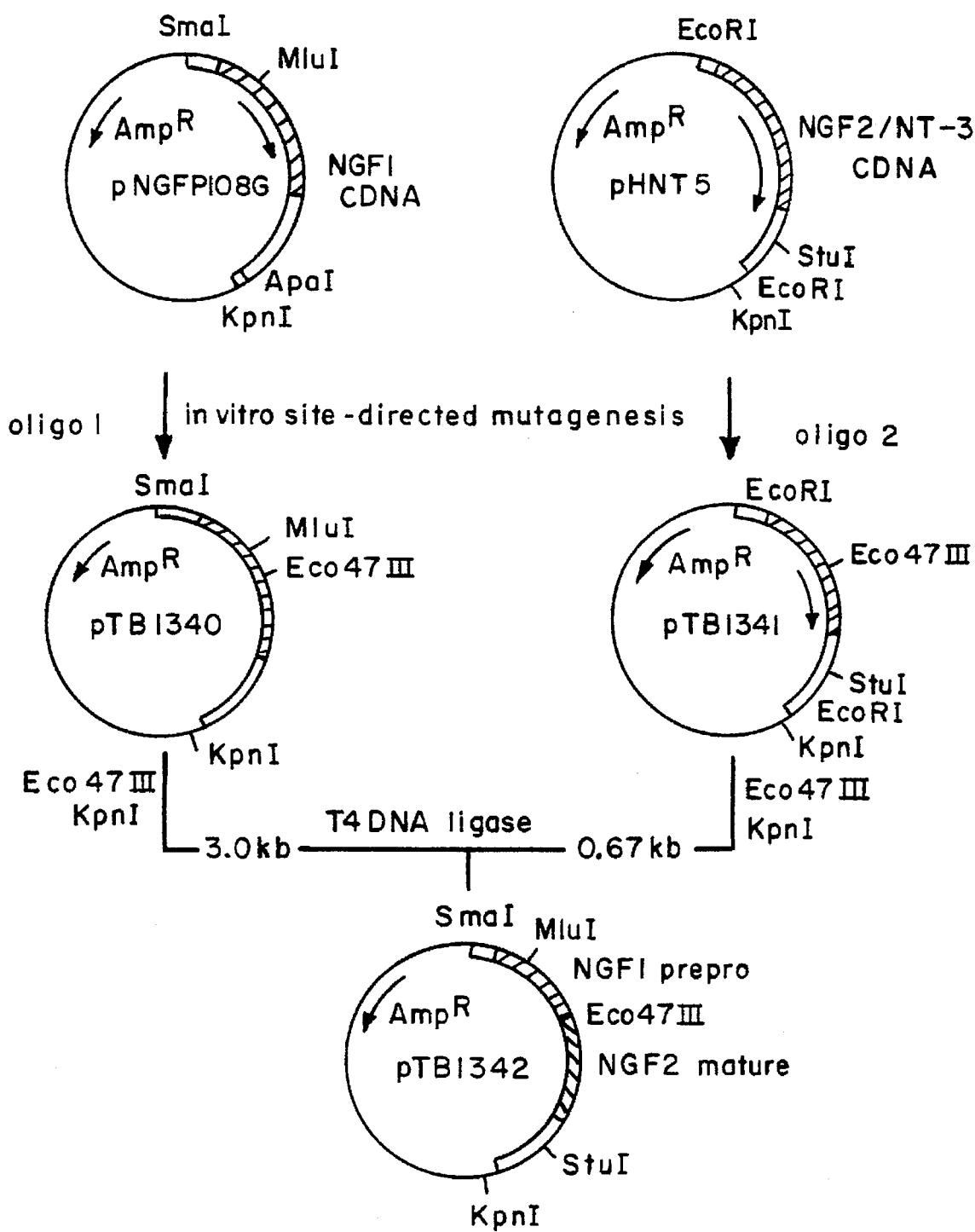
Figure 6:
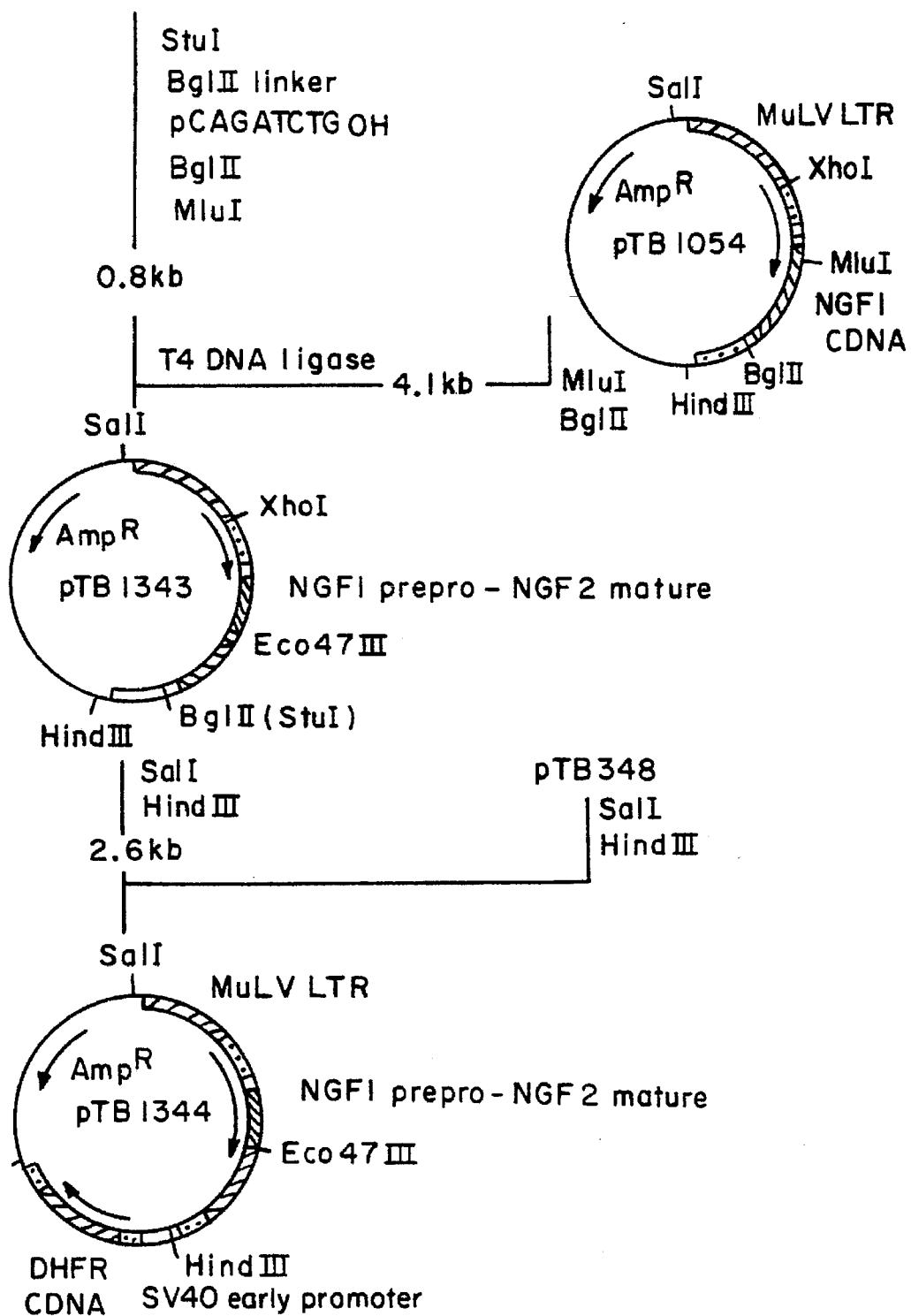

Using these oligomers, site-directed base mutations were induced to introduce the recognition site for restriction enzyme Eco47 III (AGCGCT) into each of NGF and NGF2/NT-3. This reaction was carried out using the In Vitro Mutagenesis System, Vet. 2.0 (Amershsm Corporation, UK). As a result were obtained pTB1340, a plasmid having an Eco47 III site in the human NGF gene, and pTB1341, a plasmid having an Eco47 III site in the human NGF2/NT-3 gene. pTB1340 was cleaved with restriction enzymes Kpn I and Eco47 III to yield an about 3.0 kb DNA fragment. pTB1341 was cleaved with restriction enzymes Kpn I and Eco47 III to yield a 0.67 kb DNA fragment. These two fragments were ligated using T4 DNA ligase to yield pTB1342, a plasmid having a gene which codes for a hybrid protein wherein the pre-pro-region is NGF and the mature region is NGF2/NT-3. pTB1342 was cleaved with restriction enzyme Stu I and then ligated with a synthetic Bal II linker, followed by cleavage with restriction enzymes Mlu I and Bgl II to yield a 0.8 kb DNA fragment, which was inserted into an about 4.1 kb DNA fragment obtained by cleaving pTB1054 (see Reference Example 3) with restriction enzymes Mlu I and Bgl II to yield the expression plasmid pTB1343 (see FIGS. 4 through 6). This expression plasmid was further cleaved with Sal I and Hind III to yield an about 2.6 kb DNA fragment, which was inserted into pTB348 at the Sal I-Hind III site to yield pTB1344 (see FIGS. 4 through 6).

FIG. 8 (SEQ ID NO: 9) shows the DNA which codes for the pro-region of NGF, the DNA which codes for NGF2/NT-3 and the vicinity DNA on the plasmid pTB1344.

EXAMPLE 2

Transformation and cloning of CHO cells

Hamster CHO cells (DHFR$^-$) were seeded at 4×10$^5$/petri dish to Falcon petri dishes (6 cm diameter) containing Ham F-12 medium containing 5% fetal bovine serum. After cultivation overnight at 37° C. in the presence of 5% $CO_2$, the medium was replaced with fresh medium, followed by cultivation for 4 more hours. Then, the human NGF2/NT-3 expression plasmids pTB1059, pTB1339 and pTB1344 obtained in Example 1 were each introduced to CHO cells at 10 μg per petri dish by the calcium phosphate method (Graham et al., Virology, 52, 456–467 (1973)). After 4 hours of cultivation, the medium was replaced with fresh medium and cultivation was continued overnight. Then, the medium was replaced with a selection medium (5% fetal bovine serum-Dulbecco's modified MEM-50 μg/ml kanamycin-35 μg/ml proline) and cultivation was continued. 10 to 15 days later, the cells which had become $DHFR^+$ formed a colony; single colony isolation was conducted for cloning.

EXAMPLE 3

Expression of human NGF2/NT-3 gene in transformant

Culture supernatant of the CHO transformant obtained in Example 2 was collected and assayed for human NGF2/NT-3 activity by the method described in Reference Example 5. As a result, bioactivity determined whether pTB1059, pTB1339 or pTB1344 was used for transformation.

EXAMPLE 4

Establishment of CHO cell line showing high productivity for human NGF2/NT-3

The transformants obtained in Examples 2 and 3 were each cultivated in a selection medium containing 100 nM methotrexate (described in Example 2). The clones which grew in this medium were further cultivated while step by step increasing the methotrexate concentration in the selection medium from 1 μM to 10 μM. As a result, they were obtained A1002, a cell line transformed by plasmid pTB1059, CHO-dN2-17 and CHO-dN2-19, cell lines transformed by plasmid pTB1339 and CHO-N2-1 (IFO 50307, FERM BP-3255) and CHO-N2-37, cell lines transformed by plasmid pTB1344. The amounts of NGF2/NT-3 produced by these cell lines are as follows.

In the table below, the amount of production was calculated as mouse β-NGF equivalence by the method of bioassay described in Reference Example 5. In this case, the limiting dilution point was set at 0.02 ng/ml β-NGF equivalence.

| Cell line | Amount of production |
| --- | --- |
| A1002 | 2 μg/L |
| CHO-dN2-17 | 20 μg/L |
| CHO-dN2-19 | 20 μg/L |
| CHO-N2-1 | 100 μg/L |
| CHO-N2-37 | 100 μg/L |

EXAMPLE 5

Isolation of human NGF2/NT-3

The cell line CHO-N2-1 obtained in Example 1 was seeded at $2 \times 10^4$ cells/cm$^2$ in Dulbecco's modified medium containing 5% fetal bovine serum, 35 μg/ml proline, 50 μg/ml kanamycin and 2 μM methotrexate and cultivated for 7 days at 37° C. in the presence of 5% $CO_2$. Bioassay for activity for arian embryonic DRG revealed that over 10 μg $NGF^{-1}$ equivalence of recombinant human NGF2/NT-3 was produced in this medium. The culture broth was stored at −20° C. until use.

One liter of lyophilized culture supernatant was centrifuged at 8,000 rpm, 4° C. for 15 minutes or filtered (Toyo Filter Paper No. 2) to remove cell debris and then adjusted to a final concentration of 1 mM EDTA and 0.05% CHAPS and corrected to a pH of 6.0 with 2N acetic acid. This solution was again centrifuged or filtered to remove the insoluble fraction, after which it was passed through a cation exchange resin. The cation exchange resin used was S-Sepharose Fast Flow (Pharmacia LKB, Sweden), equilibrated with 0.1M sodium phosphate buffer, pH 6.0, 1 mM EDTA and 0.05% CHAPS and packed in a column of 2.6 cm in diameter and 10 cm in height. The prepared culture supernatant was passed through this column at a flow rate of 60 ml/hr at 4° C. for adsorption. After adsorption, the column was washed with 0.1M sodium phosphate buffer, pH 6.0, 1 mM EDTA and 0.05% CHAPS at a flow rate of 60 ml/hr for 4 hours, followed by elution while flowing 0.5M NaCl, 0.1M sodium phosphate, pH 6.0, 1 mM EDTA and 0.05% CHAPS at a flow rate of 50 ml/hr. The fraction containing human NGF2/NT-3 was detected by Western blotting using the anti-polypeptide (I) N-terminal peptide antibody described in Reference Example 1 of European Patent Publication No. 386,752, collected and about 20 fold concentrated using Ultrafree 20 (Millipore, USA). The resulting concentrate was subjected to gel filtration through a column (1.6 cm dia.×8.5 cm) of Sephacryl S-100HR (Pharmacia LKB, Sweden) equilibrated with 20 mM Tris-HCl, pH 7.4, 0.15M NaCl, 1 mM EDTA and 0.05% CHAPS. In the same manner as above, the fraction containing human NGF2/NT-3 was detected by Western blotting and about 20 fold concentrated with Ultrafree 20. The resulting concentrate was applied to reverse phase HPLC to purify human NGF. Specifically, the concentrate was passed through a column of Asahipak ODP-50 (Asahi Chemical Industry Co., Ltd., Japan, 8 mm dia.×150 mm) and extracted on a density gradient of 0–90% acetonitrile containing 0.1% trifluoroacetic acid (TFA) to yield about 60 μg of purified human NGF2/NT-3.

Figure 9:
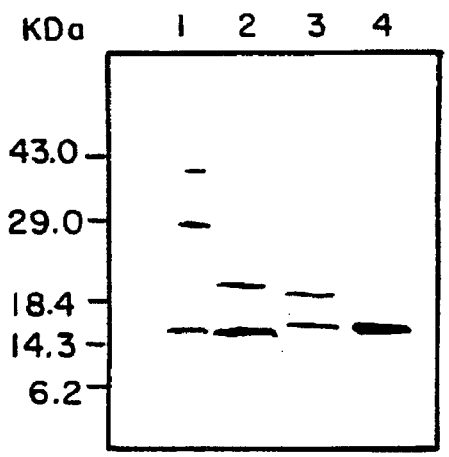
FIG. 9 shows the SDS-PAGE result obtained in Example 5.

The recombinant human NGF2/NT-3 thus obtained was assayed by SDS-PAGE (15%, 35.1:1); an almost single band appeared near the position corresponding to a molecular weight of 14,000 (FIG. 9). This reacted with the antibody described in Reference Example 1 of EP 386,752 (FIG. 10).

Figure 10:
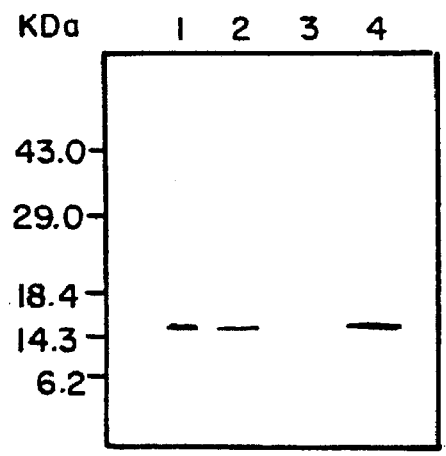
FIG. 10 shows the SDS-PAGE result obtained in Example 5.

To describe this purification process, FIG. 9 shows the silver staining pattern of SDS-PAGE assay and FIG. 10 shows the results of Western blotting following SDS-PAGE. In FIGS. 9 and 10, lane 1 shows the results for the polypeptide (I) obtained by the method described in European Patent Publication No. 386,752, lane 2 is for the sample subjected to reverse phase chromatography in Example 5, lane 3 is for the effluent fraction in reverse chromatography, lane 4 is for the fraction (NGF2/NT-3 fraction) eluted via acetonitrile density gradient elution in reverse phase chromatography.

EXAMPLE 6

Expression of human NGF2/NT-3 gene in animal cells (II)

Figure 11:
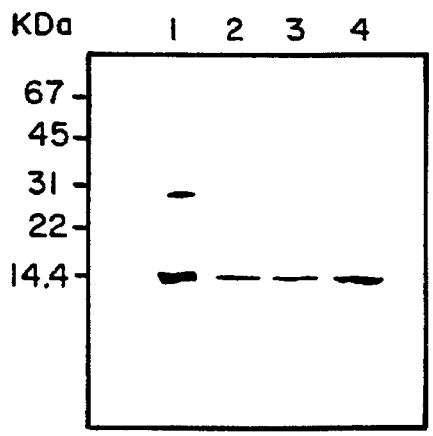
FIG. 11 shows the SDS-PAGE results obtained in Example 6.

With respect to the plasmids pTB1059 and pTB1339 which are obtained in Reference Example 4 and pTB1334 which is obtained in Example 1, expression in simian COS-7 cells was investigated. Gene introduction was achieved by the calcium phosphate method described in Example 2. The medium used was Dulbecco's modified MEM medium containing 10% fetal bovine serum, which was replaced with Dulbecco's modified MEM medium containing 0.5% fetal bovine serum after gone introduction. At 48 hours following gene introduction, the medium was collected. To 100 µl of the culture supernatant was added 10 µl of 100% (w/v) trichloroacetic acid, followed by cooling at 0° C. for 10 minutes to precipitate the protein, which was electrophoresed on SDS-PAGE. After Western blotting by a conventional method, the anti-polypeptide (I) N-terminal peptide antibody described in Reference Example 1 of EP-A-386,752 was used to detect the transformant (FIG. 11). In this system, pTB1339 produced most recombinants. In FIG. 11, lane 1 shows the results for the polypeptide I obtained by the method described in EP-A-386,752, lane 2 is for the COS supernatant from plasmid pTB1059, lane 3 is for the COS supernatant from plasmid pTB1344 and lane 4 is for the COS supernatant from plasmid pTB1339.

EXAMPLE 7

The CHO-N2-1 strain obtained in Example 1 was subjected to mass culture in the same manner as in Example 5 except that the following modifications were made.

The strain was seeded at a density of $2 \times 10^4/cm^2$ in Dulbecco's modified MEM medium containing 5% fetal bovine serum, 35 µg/ml proline, 50 µg/ml kanamycin and 2 µM methotrexate and cultivated for 7 days at 37° C. in the presence of 5% $CO_2$. After collecting the culture supernatant, the medium was replaced with Dulbecco's modified 1MEM medium/Ham F-12 medium (1:1 mixture) containing 1% fetal bovine serum, 35 µg/ml proline, 50 µg/ml kanamycin and 2 µM methotrexate (hereinafter referred to as preparation medium), followed by 3 to 4 days of cultivation. After collecting this culture supernatant, cultivation was continued for 3 to 4 days in the preparation medium, and the resulting culture supernatant was collected. From 120 petri dishes of 10 cm in diameter, a total of 5 liters of culture supernatant was obtained through this cultivation series. This procedure was twice repeated to yield 10 liters of culture supernatant, which was stored at −20° C.

Figure 12:
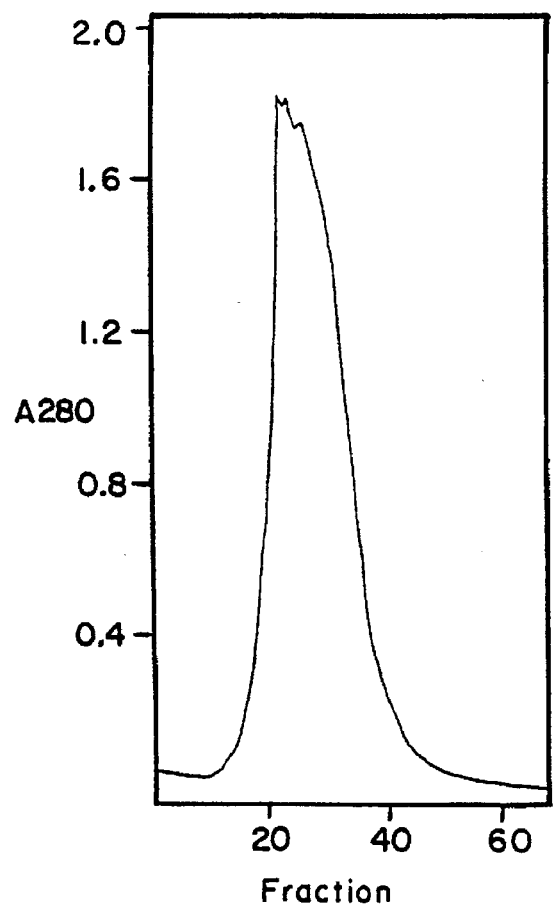
FIG. 12 shows the S-Sepharose column eluted fraction of the CHO-N2-1 strain culture supernatant obtained in Example 7.
Figure 13:
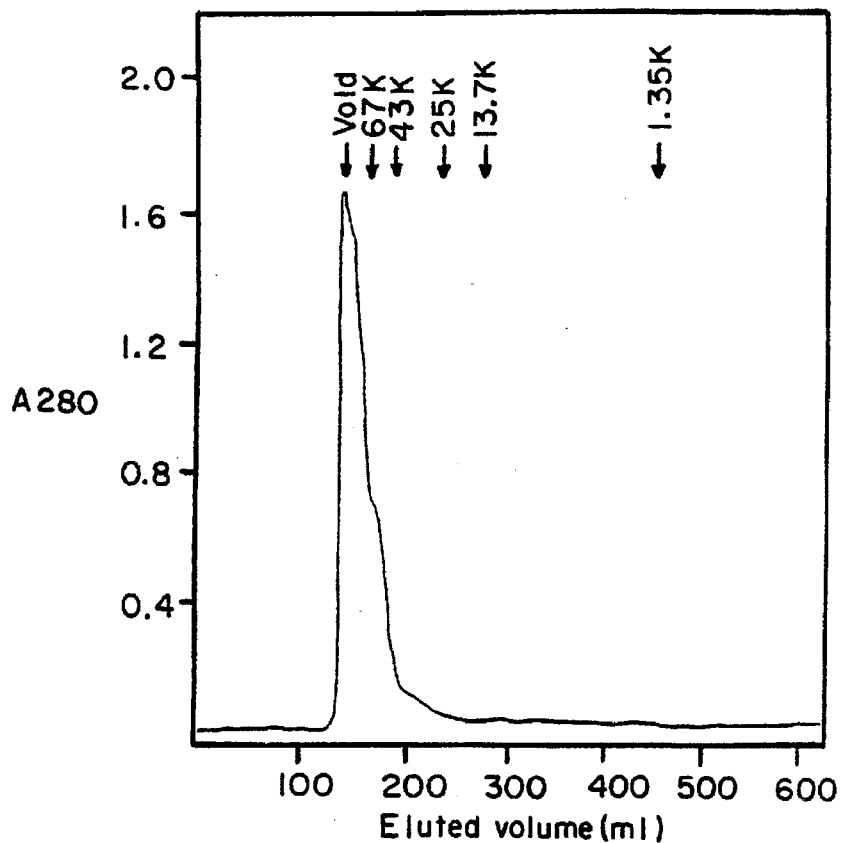
FIG. 13 shows the gel filtration eluted fraction obtained in Example 7.
Figure 14:
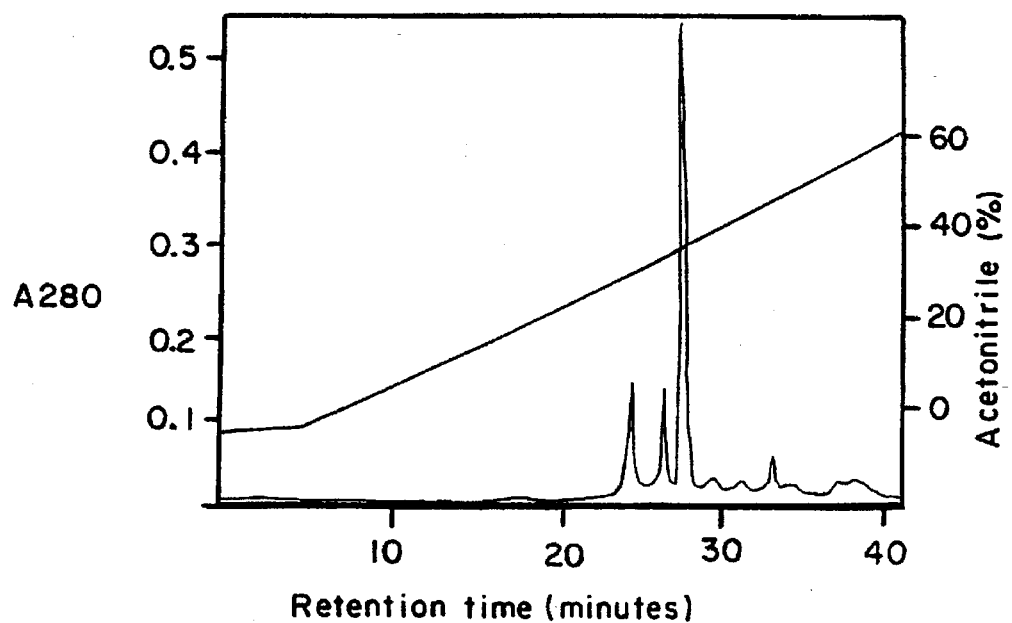
FIG. 14 shows the results of reverse phase chromatography obtained in Example 7.
Figure 15:
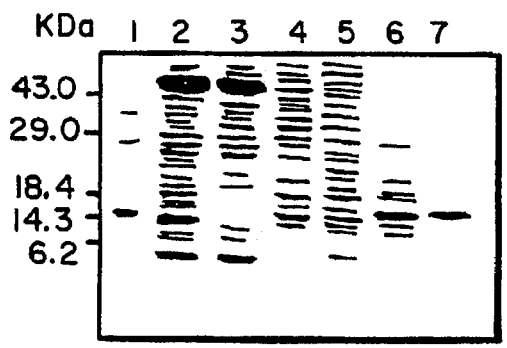
FIG. 15 shows the SDS-PAGE results of the products from respective purification processes obtained in Example 7.
Figure 16:
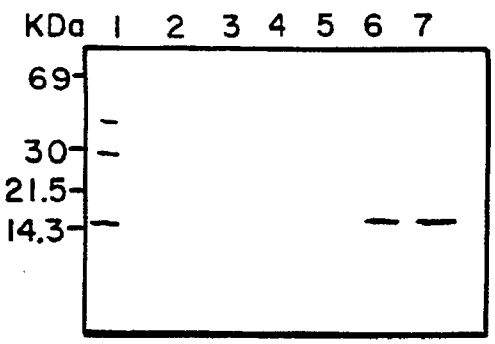
FIG. 16 shows the SDS-PAGE result obtained in Example 7.

The culture supernatant was treated as directed in Example 5 and applied to a column of S-Sepharose (5 cm dia.×20 cm). The active fraction was eluted as directed in Example 5 for 12 ml/fraction (FIG. 12). To this fraction was added ammonium sulfate to 50% saturation, and the mixture was kept standing at 0° C. for 2 hours and centrifuged at 10,000 rpm, 4° C. for 15 minutes using Sorval SS34 rotor (USA). The precipitate was collected and dissolved in 40 ml of a mixture of 20 ELM Tris-HCl (pH 7.4), 1 mM EDTA and 0.05% CHAPS. Centrifugation (15,000 rpm, 15 minutes, 4° C., Sorval SS34 rotor) was conducted to remove the insoluble substances, followed by gel filtration conducted as directed in Example 1. The column used had a size of 2.6 cm dia.×90 cm, flow rate was 100 ml/hr, sample volume was 10 ml (FIG. 13). The eluted fraction was concentrated using Ultrafree 20 (Millipore, USA) and then purified by reverse phase chromatography as directed in Example 5 (1 ml/fraction) (FIG. 14). The progress of purification in these steps is shown in Table 1. FIGS. 15 and 16 show the results of SDS-PAGE assay of these fractions. The finally obtained standard preparation gave an almost single band. Eventually, the recombinant standard preparation was obtained in an amount of 210 µg from about 10 liters of culture supernatant.

FIG. 15 shows the results of silver staining; FIG. 16 shows the results of Western blotting. In FIGS. 15 and 16, lane 1 shows the results for 0.01 µg of the polypeptide (I) obtained by the method described in EP-A-386,759, lane 2 is for 10 µg of the CHO-N2-1 cell culture supernatant, lane 3 is for 10 µg of the S-Sepharose effluent, lane 4 is for 1 µg of the S-Sepharose eluted fraction, lane 5 is for 1 µg of the ammonium sulfate precipitated fraction, lane 6 is for 0.1 µg of the gel filtration eluted fraction and lane 7 is for 0.1 µg of the reverse phase HPLC eluted fraction.

At initiation of purification, the purity was about 0.001 to 0.01% of total protein, which was purified up to a final purity of over 95% (efficiency factor $10^4$ times). To demonstrate this, results of Western blotting (FIG. 16) and silver staining (FIG. 15) are given side by side.

Table 1

*1 Determined by Bradford's method.
*2 Expressed in human NGF equivalence on the basis of elongation of nerve processes of DRG.

EXAMPLE 8

Bioactivity (I) of purified recombinant protein

Figure 17:
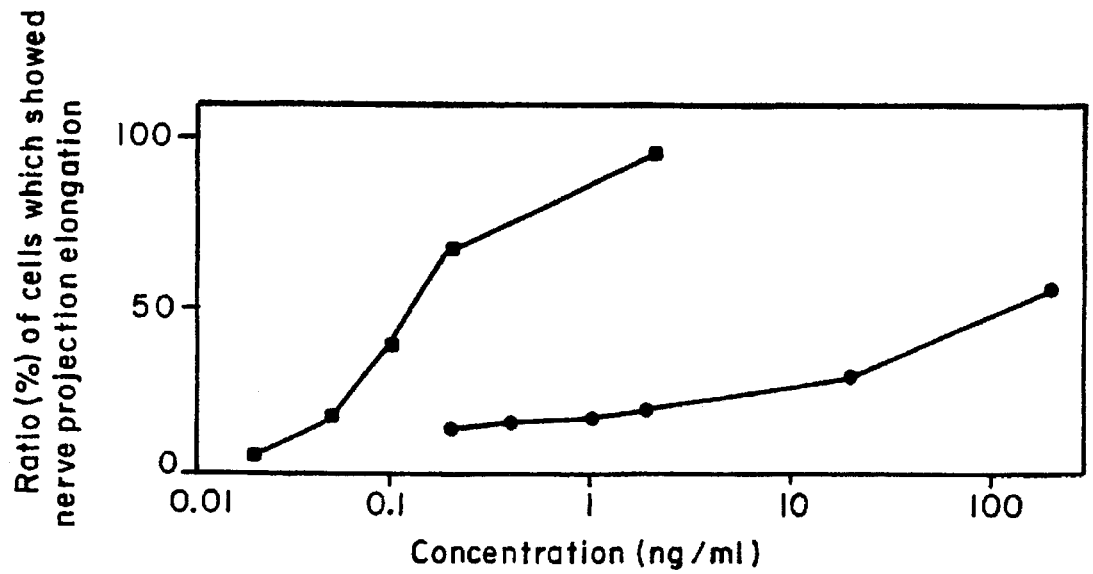
FIG. 17 shows the bioassay results obtained in Example 8.

The bioactivity of the final purified standard preparation obtained in Example 7 was determined as directed in Reference Example 5. Mouse NGFβ (Wako Pure Chemical) was used as the control. The results are shown in FIG. 17. In FIG. 17, the symbols ■ and ● show the results for mouse NGFβ and NGF2/NT-3, respectively. As seen in FIG. 17, NGF2/NT-3 was found less active than NGFβ in this system.

EXAMPLE 9

Bioactivity (II) of purified recombinant protein

Bioactivity on rat PC12 cells was determined in accordance with the method described in Biochemical and Biophysical Research Communications,

TABLE 1

| | Volume (ml) | Protein concentration (mg/ml) | Amount of protein*1 (mg) | Bioactivity*2 (µg equivalence) | Yield (%) |
| --- | --- | --- | --- | --- | --- |
| Culture supernatant | 9500 | 1.15 | 10900 | 126 | 100 |
| S-Sepharose Effluent fraction | 9500 | 1.12 | 10600 | 15 | 12 |
| 0.5 M NaCl eluted fraction | 325 | 2.00 | 700 | 49 | 38 |
| Ammonium sulfate precipitation (precipitated fraction) | 40 | 11.3 | 452 | 55 | 43 |
| Sephacryl S-100HR (concentrated fraction) | 2.5 | 0.20 | 0.50 | 33 | 26 |
| Reverse phase HPLC | 1.0 | 0.21 | 0.21 | 25 | 19 |

Figure 18:
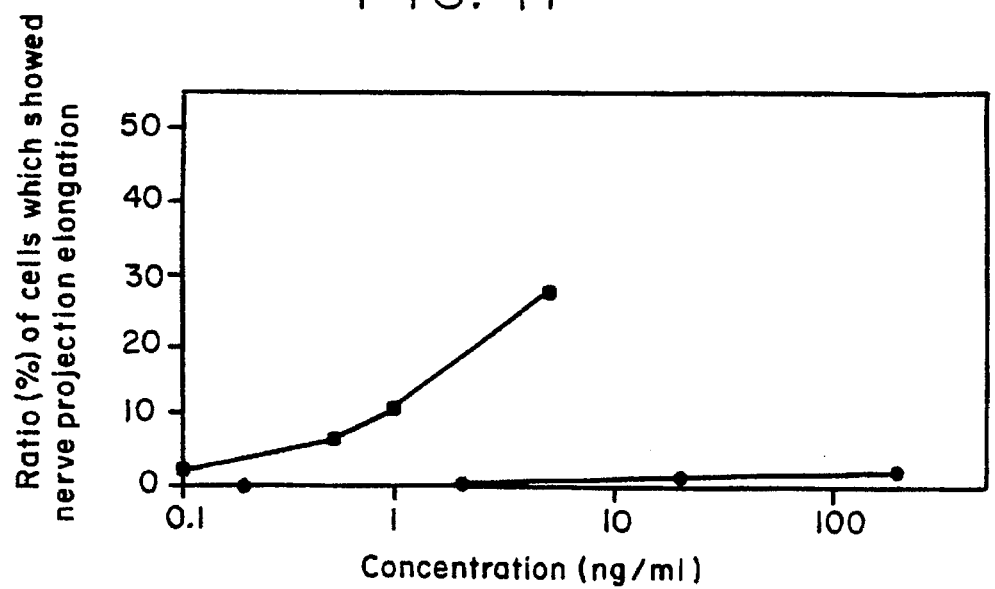
FIG. 18 shows the bioassay results obtained in Example 9.

171, 116–122 (1990). The results are shown in FIG. 18. In FIG. 18, the symbols ■ and ● show the results for mouse NGFβ and NGF2/NT-3, respectively. The recombinant NGF2 was found to be very low in nerve projection elongating activity on PC12 cells at $1/10^3$ or lower level in comparison with the activity on mouse NGFβ (Wako Pure Chemical).

EXAMPLE 10

Preparation of intact and truncated forms of NGF-2

CHO-N2-1 cells were seeded and cultured in the similar manner as described in example 5. Upon confluence the culture medium was replaced with serum-free medium (COSMEDIUM; Cosmo-Bio, Japan) and cultivation was continued for 2 days. One liter of conditioned medium was collected from a hundred of 10-cm dishes. NGF-2/NT-3 was purified in the similar manner as described in Example 5 while 0.5 mM PMSF and 1 mM benzamidine were included in collected conditioned medium and column buffers. The reversed phase HPLC gave three peaks at 24 (P1), 26 min (P2) and 28 min (P3) of retention time (FIG. 19). Both P2 and P3 had biological activity on chick embryo DRG reuron while P1 did not. P2 protein comigrated with recombinant NGF-2 produced in E. coli while P3 protein migrated slightly faster than those (FIG. 20(B)). Only P2 protein was recognized by anti-polypeptide (1) N-terminal peptide antibody (Reference Example 2 of EP-A-386,752) in Western blotting (FIG. 20(A).

In FIG. 20(A), lane (a) shows NGF-2 produced in recombinant E. coli, lane (b) shows the fraction 24 (P1) obtained by reversed phase HPLC chromatography (FIG. 19), lane (c) shows the fraction 26 (P2) obtained by reversed phase HPLC chromatography (FIG. 19), and lane (d) shows the fraction 28 (P3) obtained by reversed phase HPLC chromatography (FIG. 19).

In FIG. 20(B), lane (e) shows NGF-2 produced in recombinant E. coli, lane (f) shows the fraction 25 obtained by reversed phase HPLC chromatography (FIG. 19), lane (g) shows the fraction 26 (P2) obtained by reversed phase HPLC chromatography (FIG. 19), lane (h) shows the fraction 27 obtained by reversed phase HPLC chromatography (FIG. 19), lane (i) shows the fraction 28 (P3) obtained by reversed phase HPLC chromatography (FIG. 19), and lane (j) shows the fraction 29 obtained by reversed phase HPLC chromatography (FIG. 19).

Amino-terminal amino acid sequencing revealed that P2 and P3 correspond to full-length and amino-terminal truncated forms of mature-type NGF-2/NT-3 (Table 2).

TABLE 2

| Cycles | PTH-amino acid P2 | detected P3 | amino acid sequence predicted from cDNA |
|---|---|---|---|
| 1 | Tyr | Ser | Tyr |
| 2 | Ala | His | Ala |
| 3 | Glu | Arg | Glu |
| 4 | His | Gly | His |
| 5 | Lys | Glu | Lys |
| 6 | Ser | Tyr | Ser |
| 7 | His | Ser | His |
| 8 | Arg | Val | Arg |
| 9 | Gly | — | Gly |
| 10 | Glu | Asp | Glu |
| 11 | ND | Ser | Tyr |
| 12 | ND | Glu | Ser |
| 13 | ND | Ser | Val |
| 14 | ND | Leu | Cys |
| 15 | ND | Trp | Asp |

ND: not determined

The following references, which are referred to for their disclosures at various points in this application, are incorporated herein by reference.

Annual New York Academy of Science, 55, 330 (1952)
Proc. Natl. Acad. Sci. USA, 40, 1014 (1954)
EMBO Journal 1, 549–553 (1982)
Neurochem. 49, 705–713 (1987)
EP-A-386,752
FEBS Letters, 266, 187–191 (1990)
Nature, 344, 399 (1990)
Neuron 4, 767–773 (1990)
Science, 247, 1446–1451 (1990)
Pro. Natl. Acad. Sci. USA, 87, 5454–5458 (1990)
Nature, 303, 821–825 (1983)
J. Neurosci. Res. 20, 403–410 (1988)
Nature, 302, 538–540 (1983)
EMBO Journal, 5, 1489–1493 (1986)
Molecular Cloning, A Laboratory Mannual, Cold Spring Harbor Laboratory (1982)
Virology, 52, 456 (1973)
Journal of Molecular Biology, 159, 601 (1982)
Virology, 52, 456 (1973)
Jikken Igaku (Experimental Medicine), extra issue, vol. 5, No. 11 (1987)
Science, 122, 501 (1952)
Virology, 8, 396 (1959)
Journal of American Medical Association, 199, 519 (1967)
Proceedings of the Society of Experimental Biological Medicine, 73, 1 (1950)
Journal of Bacteriology, 153, 163 (1983)
Proc. Natl. Acad. Sci. USA, 75, 1927 (1978)
American Journal of Botany, 30, 206 (1943)
Journal of Bacteriology, 113, 727 (1973)
Saibo Seicho Inshi (Growth Factor) edited by the Japanese Tissue Culture Association, Asakura Shoten (1984)
Advanced Bacterial Genetics, Cold Spring Harbor Laboratory, 1980
Science, 209, 1422 (1980)
Nature, 294, 228 (1981)
Japanese Patent Application Laid-open No. 63282/1986
EP-A-172,619
Cell Struct. Funct. 12, 205 (1987)
Biochem. Biophys. Res. Commun. 171, 116–122 (1990)

---

What we claim is:

1. A recombinant vector comprising;
   (a) a DNA which codes for human nerve growth factor 2,
   (b) a DNA which comprises a nucleotide sequence TAGCTTGCCGCCACC, which is represented by nucleotides 1–15 of SEQ ID NO: 9,
   (c) a DNA which codes for a signal peptide of human nerve growth factor, and
   (d) a DNA which codes for a pro-region of human nerve growth factor, wherein the signal and pro-region DNA is located at the 5'-terminal of the DNA which codes for human nerve growth factor 2 and the DNA which comprises the nucleotide sequence TAGCTTGCCGCCACC, which is represented by nucleotides 1–15 is SEQ ID NO: 9, is located upstream of the DNA which codes for the signal peptide of human nerve growth factor.

2. The recombinant vector in accordance with claim 1, wherein the DNA which codes for the pro-region of human nerve growth factor encodes the amino acid sequence: Glu Pro His Ser Glu Ser Asn Val Pro Ala Gly His Thr Ile Pro Gln Val His Trp Thr Lys Leu Gln His Ser Leu Asp Thr Ala Leu Arg Arg Ala Arg Ser Ala Pro Ala Ala Ala Ile Ala Ala Arg Val Ala Cly Gln Thr Arg Asn Ile Thr Val Asp Pro Ala Leu Phe Lys Lys Arg Arg Leu Arg Ser Pro Ara Val Leu Phe Ser Thr Gln Pro Pro Arg Glu Ala Ala Asp Thr Gln Asp Leu Asp Phe Glu Val Gly Gly Ala Ala Pro Phe Asn Arg Thr His Arg Ser Lys Arg (SEQ ID No:10).

3. A transformant obtained from inserting the vector of claim 1 into a host.

4. The transformant of claim 3, wherein the host is selected from a group consisting of an animal cell and yeast.

5. The transformant of claim 3, wherein the host is an animal call selected from a group consisting of simian Vero cells, human Hera cells, Chinese hamster (CHO) cells, mouse L cello, mouse C127 cells, mouse BALB/3T3 Cells and lymphocytes.

6. The recombinant vector in accordance with claim 1, wherein the DNA which codes for the human nerve growth factor 2 encodes the amino acid sequence of amino acids 1 to 119 of SEQ ID NO:9.

7. The recombinant vector in accordance with claim 1, wherein the DNA which codes for the signal peptide of human nerve growth factor encodes the amino acid sequence of amino acids –121 to –104 of SEQ ID NO:9.

8. A method of using a transformant to produce nerve growth factor 2, which comprises cultivating a transformant harboring a recombinant vector containing
  (a) a DNA which code for human nerve growth factor 2,
  (b) a DNA which comprises the nucleotide sequence TAGCTTGCCGCCACC, which is represented by nucleotides 1–15 of SEQ ID NO:9,
  (c) a DNA which code for the signal peptide of human nerve growth factor, and
  (d) a DNA which code for the pro-region of human nerve growth factor, wherein the signal and pro-region DNA is located at the 5'-terminal of DNA which codes for human nerve growth factor 2, and the DNA which comprises the nucleotide sequence represented by TAGCTTGCCGCCACC, which is represented by nucleotides 1–15 of SEQ ID NO:9, is located upstream of the DNA which code for the signal peptide of human nerve growth factor, under conditions suitable for expression of human nerve growth factor 2.

9. A recombinant vector comprising a DNA represented by the nucleotide sequence of nucleotides 1 to 735 of SEQ ID NO.9.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: Synthetic DNA ( i i i ) HYPOTHETICAL: NO ( i v ) ANTI-SENSE: NO ( x i ) SEQUENCE DESCRIPTION: SEQ ID NO:1:

AGCTTGCCGC CACCATGTCC ATGTTGTTCT ACACTCT                              37

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: YES ( x i ) SEQUENCE DESCRIPTION: SEQ ID NO:2:

GATCAGAGTG TAGAACAACA TGGACATGGT GGCGGCA                              37

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( x i ) SEQUENCE DESCRIPTION: SEQ ID NO:3:

CAGATCTGGG CC                                                         12

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( x i ) SEQUENCE DESCRIPTION: SEQ ID NO:4:

TACAGGTGAA TTCGGCCATG TCCATCTTG                                       29

( 2 ) INFORMATION FOR SEQ ID NO:5:

( i ) SEQUENCE CHARACTERISTICS:
        ( A ) LENGTH: 23 base pairs
        ( B ) TYPE: nucleic acid (C) STRANDEDNESS: single
(D) TOPOLOGY: linear (ii) MOLECULE TYPE: Synthetic DNA (iii) HYPOTHETICAL: NO (iv) ANTI-SENSE: YES (xi) SEQUENCE DESCRIPTION: SEQ ID NO:5:

AGAGATGCGA ATTCATGTTC TTC    23

(2) INFORMATION FOR SEQ ID NO:6:

(i) SEQUENCE CHARACTERISTICS:
 (A) LENGTH: 969 base pairs
 (B) TYPE: nucleic acid
 (C) STRANDEDNESS: double
 (D) TOPOLOGY: linear (ii) MOLECULE TYPE: DNA (genomic)

(iii) HYPOTHETICAL: NO (vi) ORIGINAL SOURCE:
 (A) ORGANISM: HUMAN
 (G) CELL TYPE: LEUKOCYTE (ix) FEATURE:
 (A) NAME/KEY:CDS
 (B) LOCATION:11..781

(ix) FEATURE:
 (A) NAME/KEY: mat peptide
 (B) LOCATION: 425..781

(xi) SEQUENCE DESCRIPTION: SEQ ID NO:6:

| | | | | | | | | | | | | | | |
|---|---|---|---|---|---|---|---|---|---|---|---|---|---|---|
| GAATTCGGCC | ATG | TCC | ATC | TTG | TTT | TAT | GTG | ATA | TTT | CTC | GCT | TAT | CTC | 49 |
| | Met -138 | Ser | Ile | Leu -135 | Phe | Tyr | Val | Ile | Phe -130 | Leu | Ala | Tyr | Leu | |
| CGT | GGC | ATC | CAA | GGT | AAC | AAC | ATG | GAT | CAA | AGG | AGT | TTG | CCA | GAA | GAC | 97 |
| Arg -125 | Gly | Ile | Gln | Gly | Asn -120 | Asn | Met | Asp | Gln | Arg -115 | Ser | Leu | Pro | Glu | Asp -110 | |
| TCG | CTC | AAT | TCC | CTC | ATT | ATT | AAG | CTG | ATC | CAG | GCA | GAT | ATT | TTG | AAA | 145 |
| Ser | Leu | Asn | Ser | Leu -105 | Ile | Ile | Lys | Leu | Ile -100 | Gln | Ala | Asp | Ile | Leu -95 | Lys | |
| AAC | AAG | CTC | TCC | AAG | CAG | ATG | GTG | GAC | GTT | AAG | GAA | AAT | TAC | CAG | AGC | 193 |
| Asn | Lys | Leu | Ser -90 | Lys | Gln | Met | Val | Asp -85 | Val | Lys | Glu | Asn | Tyr -80 | Gln | Ser | |
| ACC | CTG | CCC | AAA | GCT | GAG | GCT | CCC | CGA | GAG | CCG | GAG | CGG | GGA | GGG | CCC | 241 |
| Thr | Leu | Pro -75 | Lys | Ala | Glu | Ala | Pro -70 | Arg | Glu | Pro | Glu | Arg -65 | Gly | Gly | Pro | |
| GCC | AAG | TCA | GCA | TTC | CAG | CCA | GTG | ATT | GCA | ATG | GAC | ACC | GAA | CTG | CTG | 289 |
| Ala | Lys -60 | Ser | Ala | Phe | Gln | Pro -55 | Val | Ile | Ala | Met | Asp -50 | Thr | Glu | Leu | Leu | |
| CGA | CAA | CAG | AGA | CGC | TAC | AAC | TCA | CCG | CGG | GTC | CTG | CTG | AGC | GAC | AGC | 337 |
| Arg -45 | Gln | Gln | Arg | Arg | Tyr -40 | Asn | Ser | Pro | Arg | Val -35 | Leu | Leu | Ser | Asp | Ser -30 | |
| ACC | CCC | TTG | GAG | CCC | CCG | CCC | TTG | TAT | CTC | ATG | GAG | GAT | TAC | GTG | GGC | 385 |
| Thr | Pro | Leu | Glu | Pro -25 | Pro | Pro | Leu | Tyr | Leu -20 | Met | Glu | Asp | Tyr | Val -15 | Gly | |
| AGC | CCC | GTG | GTG | GCG | AAC | AGA | ACA | TCA | CGG | CGG | AAA | CGG | TAC | GCG | GAG | 433 |
| Ser | Pro | Val | Val -10 | Ala | Asn | Arg | Thr | Ser -5 | Arg | Arg | Lys | Arg | Tyr 1 | Ala | Glu | |
| CAT | AAG | AGT | CAC | CGA | GGG | GAG | TAC | TCG | GTA | TGT | GAC | AGT | GAG | AGT | CTG | 481 |
| His | Lys 5 | Ser | His | Arg | Gly | Glu 10 | Tyr | Ser | Val | Cys | Asp 15 | Ser | Glu | Ser | Leu | |

| | | | | | | | | | | | | | | | | |
|---|---|---|---|---|---|---|---|---|---|---|---|---|---|---|---|---|
| TGG | GTG | ACC | GAC | AAG | TCA | TCG | GCC | ATC | GAC | ATT | CGG | GGA | CAC | CAG | GTC | 529 |
| Trp | Val | Thr | Asp | Lys | Ser | Ser | Ala | Ile | Asp | Ile | Arg | Gly | His | Gln | Val | |
| 20 | | | | 25 | | | | | 30 | | | | | | 35 | |
| ACG | GTG | CTG | GGG | GAG | ATC | AAA | ACG | GGC | AAC | TCT | CCC | GTC | AAA | CAA | TAT | 577 |
| Thr | Val | Leu | Gly | Glu | Ile | Lys | Thr | Gly | Asn | Ser | Pro | Val | Lys | Gln | Tyr | |
| | | | | 40 | | | | | 45 | | | | | 50 | | |
| TTT | TAT | GAA | ACG | CGA | TGT | AAG | GAA | GCC | AGG | CCG | GTC | AAA | AAC | GGT | TGC | 625 |
| Phe | Tyr | Glu | Thr | Arg | Cys | Lys | Glu | Ala | Arg | Pro | Val | Lys | Asn | Gly | Cys | |
| | | | 55 | | | | | 60 | | | | | 65 | | | |
| AGG | GGT | ATT | GAT | GAT | AAA | CAC | TGG | AAC | TCT | CAG | TGC | AAA | ACA | TCC | CAA | 673 |
| Arg | Gly | Ile | Asp | Asp | Lys | His | Trp | Asn | Ser | Gln | Cys | Lys | Thr | Ser | Gln | |
| | | 70 | | | | | 75 | | | | | 80 | | | | |
| ACC | TAC | GTC | CGA | GCA | CTG | ACT | TCA | GAG | AAC | AAT | AAA | CTC | GTG | GGC | TGG | 721 |
| Thr | Tyr | Val | Arg | Ala | Leu | Thr | Ser | Glu | Asn | Asn | Lys | Leu | Val | Gly | Trp | |
| | 85 | | | | | 90 | | | | | 95 | | | | | |
| CGG | TGG | ATA | CGG | ATA | GAC | ACG | TCC | TGT | GTG | TGT | GCC | TTG | TCG | AGA | AAA | 769 |
| Arg | Trp | Ile | Arg | Ile | Asp | Thr | Ser | Cys | Val | Cys | Ala | Leu | Ser | Arg | Lys | |
| 100 | | | | | 105 | | | | | 110 | | | | | 115 | |

ATC GGA AGA ACA TGAATTGGCA TCTCTCCCCA TATATAAATT ATTACTTTAA                   821
Ile Gly Arg Thr
ATTATATGAT ATGCATGTAG CATATAAATG TTTATATTGT TTTTATATAT TATAAGTTGA            881

CCTTTATTTA TTAAACTTCA GCAACCCTAC AGTATATAGG CTTTTTCTC AATAAAATCA             941

GTGTGCTTGC CTTCCCTCAG GCAGATCT                                                969

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( x i ) SEQUENCE DESCRIPTION: SEQ ID NO:7:

TCACGGCGGA AGCGCTACGC GGAGCAT                                                27

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Synthetic DNA ( i i i ) HYPOTHETICAL: NO ( i v ) ANTI-SENSE: NO ( x i ) SEQUENCE DESCRIPTION: SEQ ID NO:8:

AGGAGCAAGC GCTCATCATC CCA                                                    23

( 2 ) INFORMATION FOR SEQ ID NO:9:

( i ) SEQUENCE CHARACTERISTICS:
        ( A ) LENGTH: 923 base pairs
        ( B ) TYPE: nucleic acid
        ( C ) STRANDEDNESS: double
        ( D ) TOPOLOGY: linear ( i i ) MOLECULE TYPE: Genomic DNA and cDNA ( i i i ) HYPOTHETICAL: NO ( v i ) ORIGINAL SOURCE:
    ( A ) ORGANISM: HUMAN
    ( B ) STRAIN: GLIOMA HS683 (cDNA)
    ( G ) CELL TYPE: LEUKOCYTE (GENOMIC DNA)

( i x ) FEATURE:
    ( A ) NAME/KEY: CDS
    ( B ) LOCATION: 16..735

( i x ) FEATURE:
    ( A ) NAME/KEY: mat peptide
    ( B ) LOCATION: 379..735

( x i ) SEQUENCE DESCRIPTION: SEQ ID NO:9:

```
TAGCTTGCCG CCACC ATG TCC ATG TTG TTC TAC ACT CTG ATC ACA GCT TTT        51
                Met Ser Met Leu Phe Tyr Thr Leu Ile Thr Ala Phe
                -121 -120              -115                  -110

CTG ATC GGC ATA CAG GCG GAA CCA CAC TCA GAG AGC AAT GTC CCT GCA        99
Leu Ile Gly Ile Gln Ala Glu Pro His Ser Glu Ser Asn Val Pro Ala
              -105              -100                      -95

GGA CAC ACC ATC CCC CAA GTC CAC TGG ACT AAA CTT CAG CAT TCC CTT       147
Gly His Thr Ile Pro Gln Val His Trp Thr Lys Leu Gln His Ser Leu
             -90              -85                      -80

GAC ACT GCC CTT CGC AGA GCC CGC AGC GCC CCG GCA GCG GCG ATA GCT       195
Asp Thr Ala Leu Arg Arg Ala Arg Ser Ala Pro Ala Ala Ala Ile Ala
         -75              -70                      -65

GCA CGC GTG GCG GGG CAG ACC CGC AAC ATT ACT GTG GAC CCC AGG CTG       243
Ala Arg Val Ala Gly Gln Thr Arg Asn Ile Thr Val Asp Pro Arg Leu
     -60              -55                      -50

TTT AAA AAG CGG CGA CTC CGT TCA CCC CGT GTG CTG TTT AGC ACC CAG       291
Phe Lys Lys Arg Arg Leu Arg Ser Pro Arg Val Leu Phe Ser Thr Gln
-45              -40                      -35                  -30

CCT CCC CGT GAA GCT GCA GAC ACT CAG GAT CTG GAC TTC GAG GTC GGT       339
Pro Pro Arg Glu Ala Ala Asp Thr Gln Asp Leu Asp Phe Glu Val Gly
             -25              -20                      -15

GGT GCT GCC CCC TTC AAC AGG ACT CAC AGG AGC AAG CGC TAC GCG GAG       387
Gly Ala Ala Pro Phe Asn Arg Thr His Arg Ser Lys Arg Tyr Ala Glu
         -10              -5                         1

CAT AAG AGT CAC CGA GGG GAG TAC TCG GTA TGT GAC AGT GAG AGT CTG       435
His Lys Ser His Arg Gly Glu Tyr Ser Val Cys Asp Ser Glu Ser Leu
     5                   10                      15

TGG GTG ACC GAC AAG TCA TCG GCC ATC GAC ATT CGG GGA CAC CAG GTC       483
Trp Val Thr Asp Lys Ser Ser Ala Ile Asp Ile Arg Gly His Gln Val
20                   25                      30                  35

ACG GTG CTG GGG GAG ATC AAA ACG GGC AAC TCT CCC GTC AAA CAA TAT       531
Thr Val Leu Gly Glu Ile Lys Thr Gly Asn Ser Pro Val Lys Gln Tyr
             40                      45                      50

TTT TAT GAA ACG CGA TGT AAG GAA GCC AGG CCG GTC AAA AAC GGT TGC       579
Phe Tyr Glu Thr Arg Cys Lys Glu Ala Arg Pro Val Lys Asn Gly Cys
             55                      60                      65

AGG GGT ATT GAT GAT AAA CAC TGG AAC TCT CAG TGC AAA ACA TCC CAA       627
Arg Gly Ile Asp Asp Lys His Trp Asn Ser Gln Cys Lys Thr Ser Gln
             70                      75                      80

ACC TAC GTC CGA GCA CTG ACT TCA GAG AAC AAT AAA CTC GTG GGC TGG       675
Thr Tyr Val Arg Ala Leu Thr Ser Glu Asn Asn Lys Leu Val Gly Trp
             85                      90                      95

CGG TGG ATA CGG ATA GAC ACG TCC TGT GTG TGT GCC TTG TCG AGA AAA       723
Arg Trp Ile Arg Ile Asp Thr Ser Cys Val Cys Ala Leu Ser Arg Lys
100              105                     110                    115

ATC GGA AGA ACA TGAATTGGCA TCTCTCCCCA TATATAAATT ATTACTTTAA           775
Ile Gly Arg Thr
```

```
ATTATATGAT  ATGCATGTAG  CATATAAATG  TTTATATTGT  TTTTATATAT  TATAAGTTGA      835

CCTTTATTTA  TTAAACTTCA  GCAACCCTAC  AGTATATAGG  CTTTTTTCTC  AATAAAATCA      895

GTGTGCTTGC  CTTCCCTCAG  GCAGATCT                                            923
```

(2) INFORMATION FOR SEQ ID NO:10:

(i) SEQUENCE CHARACTERISTICS:
        (A) LENGTH: 103 amino acids
        (B) TYPE: amino acid
        (C) STRANDEDNESS: unknown
        (D) TOPOLOGY: unknown (xi) SEQUENCE DESCRIPTION: SEQ ID NO:10:

```
Glu  Pro  His  Ser  Glu  Ser  Asn  Val  Pro  Ala  Gly  His  Thr  Ile  Pro  Gln
 1              5                        10                           15

Val  His  Trp  Thr  Lys  Leu  Gln  His  Ser  Leu  Asp  Thr  Ala  Leu  Arg  Arg
               20                        25                      30

Ala  Arg  Ser  Ala  Pro  Ala  Ala  Ala  Ile  Ala  Ala  Arg  Val  Ala  Gly  Glu
          35                         40                      45

Thr  Arg  Asn  Ile  Thr  Val  Asp  Pro  Arg  Leu  Phe  Lys  Lys  Arg  Arg  Leu
     50                         55                      60

Arg  Ser  Pro  Arg  Val  Leu  Phe  Ser  Thr  Gln  Pro  Pro  Arg  Glu  Ala  Ala
 65                       70                      75                           80

Asp  Thr  Gln  Asp  Leu  Asp  Phe  Glu  Val  Gly  Gly  Ala  Ala  Pro  Pro  Asn
                85                             90                       95

Arg  Thr  His  Arg  Ser  Lys  Arg
                100
```

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: unknown
        (D) TOPOLOGY: unknown (xi) SEQUENCE DESCRIPTION: SEQ ID NO:11:

```
ACTCACAGGA  GCAAGCGGTC  ATCATCCCAT  CCCAT                                    35
```